United States Patent
Lotter

(10) Patent No.: US 12,367,574 B2
(45) Date of Patent: Jul. 22, 2025

(54) SYSTEMS AND METHODS FOR ANALYZING TWO-DIMENSIONAL AND THREE-DIMENSIONAL IMAGE DATA

(71) Applicant: DeepHealth, Inc., Cambridge, MA (US)

(72) Inventor: William Lotter, Boston, MA (US)

(73) Assignee: DeepHealth, Inc., Cambridge, MA (US)

( * ) Notice: Subject to any disclaimer, the term of this patent is extended or adjusted under 35 U.S.C. 154(b) by 480 days.

(21) Appl. No.: 17/787,772

(22) PCT Filed: Dec. 23, 2020

(86) PCT No.: PCT/US2020/066912
§ 371 (c)(1),
(2) Date: Jun. 21, 2022

(87) PCT Pub. No.: WO2021/133954
PCT Pub. Date: Jul. 1, 2021

(65) Prior Publication Data
US 2023/0091506 A1 Mar. 23, 2023

Related U.S. Application Data

(60) Provisional application No. 62/953,033, filed on Dec. 23, 2019.

(51) Int. Cl.
*G06T 7/00* (2017.01)
*G06V 10/82* (2022.01)
(Continued)

(52) U.S. Cl.
CPC ............ *G06T 7/0012* (2013.01); *G06V 10/82* (2022.01); *G16H 30/40* (2018.01);
(Continued)

(58) Field of Classification Search
CPC ........ G06T 7/0012; G06T 2207/10112; G16H 30/40; G16H 15/00; G06V 10/82
(Continued)

(56) References Cited

U.S. PATENT DOCUMENTS 6,909,795 B2   6/2005   Tecotzky et al.
7,072,498 B1   7/2006   Roehrig et al.
(Continued)

FOREIGN PATENT DOCUMENTS

CN   110009623 A   7/2019
WO   2013123091 A1   8/2013
(Continued)

OTHER PUBLICATIONS

Debelee et al., Survey of Deep Learning in Breast Cancer Image Analysis, Evolving Systems, 2020, 11(1):143-163.
(Continued)

*Primary Examiner* — Gabriel I Garcia
(74) *Attorney, Agent, or Firm* — Quarles & Brady LLP

(57) ABSTRACT

The present disclosure provides a computerized method for a likelihood of malignancy in breast tissue of a patient. The method includes receiving, with a computer processor, an image of the breast tissue, providing the image of the breast tissue to a model including a trained neural network; the trained neural network being previously trained by training a first neural network, initializing a second neural network based on the first neural network, training the second neural network, and outputting the second neural network as the trained neural network, receiving an indicator from the model, and outputting a report including the indicator to at least one of a memory or a display.

30 Claims, 9 Drawing Sheets

(51) Int. Cl.
*G16H 30/40* (2018.01)
*G16H 15/00* (2018.01)

(52) U.S. Cl.
CPC ............. *G06T 2207/10112* (2013.01); *G06T 2207/20081* (2013.01); *G06T 2207/20084* (2013.01); *G06T 2207/30068* (2013.01); *G16H 15/00* (2018.01)

(58) Field of Classification Search
USPC ........................................................ 382/131
See application file for complete search history.

(56) References Cited

U.S. PATENT DOCUMENTS

| | | |
|---|---|---|
| 7,123,684 B2 | 10/2006 | Jing et al. |
| 7,333,645 B1 | 2/2008 | Mitchell et al. |
| 7,386,165 B2 | 6/2008 | Dundar et al. |
| 7,418,123 B2 | 8/2008 | Giger et al. |
| 7,430,272 B2 | 9/2008 | Jing et al. |
| 7,577,282 B2 | 8/2009 | Gkanatsios et al. |
| 7,616,801 B2 | 11/2009 | Gkanatsios et al. |
| 7,640,051 B2 | 12/2009 | Krishnan et al. |
| 7,668,352 B2 | 2/2010 | Tecotzky et al. |
| 7,672,494 B2 | 3/2010 | Doi et al. |
| 7,702,142 B2 | 4/2010 | Ren et al. |
| 7,760,853 B2 | 7/2010 | Jing et al. |
| 7,760,924 B2 | 7/2010 | Ruth et al. |
| 7,787,682 B2 | 8/2010 | Collins et al. |
| 7,831,296 B2 | 11/2010 | DeFreitas et al. |
| 7,840,046 B2 | 11/2010 | Jerebko et al. |
| 7,869,563 B2 | 1/2011 | Defreitas et al. |
| 7,889,896 B2 | 2/2011 | Roehrig et al. |
| 7,916,915 B2 | 3/2011 | Gkanatsios et al. |
| 7,949,091 B2 | 5/2011 | Jing et al. |
| 8,090,172 B2 | 1/2012 | Shinagawa et al. |
| 8,135,188 B2 | 3/2012 | Shinagawa et al. |
| 8,139,832 B2 | 3/2012 | Kshirsagar |
| 8,155,421 B2 | 4/2012 | Ren et al. |
| 8,175,219 B2 | 5/2012 | Defreitas et al. |
| 8,223,916 B2 | 7/2012 | Srinivas et al. |
| 8,285,020 B2 | 10/2012 | Gkanatsios et al. |
| 8,331,636 B2 | 12/2012 | Shinagawa et al. |
| 8,340,388 B2 | 12/2012 | Rosenstengel |
| 8,416,915 B2 | 4/2013 | Jing et al. |
| 8,452,379 B2 | 5/2013 | DeFreitas et al. |
| 8,565,372 B2 | 10/2013 | Stein et al. |
| 8,565,374 B2 | 10/2013 | Defreitas et al. |
| 8,565,506 B2 | 10/2013 | Marshall et al. |
| 8,571,289 B2 | 10/2013 | Ruth et al. |
| 8,634,610 B2 | 1/2014 | Kontos et al. |
| 8,634,622 B2 | 1/2014 | Woods et al. |
| 8,712,127 B2 | 4/2014 | Ren et al. |
| 8,768,026 B2 | 7/2014 | Ren et al. |
| 8,831,171 B2 | 9/2014 | Jing et al. |
| 8,897,535 B2 | 11/2014 | Ruth et al. |
| 8,983,156 B2 | 3/2015 | Periaswamy et al. |
| 9,042,612 B2 | 5/2015 | Gkanatsios et al. |
| 9,066,706 B2 | 6/2015 | DeFreitas et al. |
| 9,084,579 B2 | 7/2015 | Ren et al. |
| 9,095,306 B2 | 8/2015 | Gkanatsios et al. |
| 9,456,797 B2 | 10/2016 | Ruth et al. |
| 9,460,508 B2 | 10/2016 | Gkanatsios et al. |
| 9,498,175 B2 | 11/2016 | Stein et al. |
| 9,549,709 B2 | 1/2017 | DeFreitas et al. |
| 9,792,703 B2 | 10/2017 | Costa et al. |
| 9,808,215 B2 | 11/2017 | Ruth et al. |
| 9,811,758 B2 | 11/2017 | Ren et al. |
| 9,851,888 B2 | 12/2017 | Gkanatsios et al. |
| 9,892,343 B2 | 2/2018 | Ragusa et al. |
| 10,008,184 B2 | 6/2018 | Kreeger et al. |
| 10,010,302 B2 | 7/2018 | Ruth et al. |
| 10,108,329 B2 | 10/2018 | Gkanatsios et al. |
| 10,111,632 B2 | 10/2018 | Anavi et al. |
| 10,194,875 B2 | 2/2019 | DeFreitas et al. |
| 10,242,490 B2 | 3/2019 | Karssemeijer et al. |
| 10,248,882 B2 | 4/2019 | Ren et al. |
| 10,296,199 B2 | 5/2019 | Gkanatsios et al. |
| 10,398,398 B2 | 9/2019 | Ren et al. |
| 10,413,255 B2 | 9/2019 | Stein et al. |
| 10,413,263 B2 | 9/2019 | Ruth et al. |
| 10,424,411 B2 | 9/2019 | El-Zehiry |
| 10,452,252 B2 | 10/2019 | Gkanatsios et al. |
| 10,565,707 B2 | 2/2020 | Liu et al. |
| 10,573,276 B2 | 2/2020 | Kreeger et al. |
| 10,580,137 B2 | 3/2020 | Amit et al. |
| 10,638,994 B2 | 5/2020 | DeFreitas et al. |
| 10,679,095 B2 | 6/2020 | Ren et al. |
| 10,687,776 B2 | 6/2020 | Suri et al. |
| 10,702,233 B2 | 7/2020 | Pauly |
| 10,719,223 B2 | 7/2020 | Gkanatsios et al. |
| 10,762,624 B2 | 9/2020 | Daughton et al. |
| 10,779,785 B2 | 9/2020 | Itu et al. |
| 10,905,385 B2 | 2/2021 | DeFreitas et al. |
| 10,952,692 B2 | 3/2021 | Ren et al. |
| 10,959,694 B2 | 3/2021 | Jing et al. |
| 10,978,026 B2 | 4/2021 | Kreeger et al. |
| 11,096,644 B2 | 8/2021 | DeFreitas et al. |
| 11,106,950 B2 | 8/2021 | Kecskemethy et al. |
| 11,205,265 B2 | 12/2021 | Hall et al. |
| 11,399,790 B2 | 8/2022 | Chui et al. |
| 2008/0152086 A1 | 6/2008 | Hall et al. |
| 2009/0082637 A1 | 3/2009 | Galperin |
| 2010/0128950 A1 | 5/2010 | Woods et al. |
| 2014/0376690 A1 | 12/2014 | Jing et al. |
| 2018/0047211 A1 | 2/2018 | Chen et al. |
| 2018/0075628 A1 | 3/2018 | Teare |
| 2018/0232883 A1 | 8/2018 | Sethi et al. |
| 2018/0289347 A1 | 10/2018 | DeFreitas et al. |
| 2019/0005684 A1 | 1/2019 | De Fauw et al. |
| 2019/0090834 A1 | 3/2019 | Pauly |
| 2019/0130562 A1 | 5/2019 | Liu et al. |
| 2019/0209116 A1 | 7/2019 | Sjostrand et al. |
| 2019/0236782 A1 | 8/2019 | Amit et al. |
| 2019/0318474 A1 | 10/2019 | Han |
| 2020/0348835 A1 | 11/2020 | Gkanatsios et al. |
| 2021/0125334 A1 | 4/2021 | Lotter |
| 2021/0128087 A1 | 5/2021 | DeFreitas et al. |
| 2021/0204894 A1 | 7/2021 | Ren et al. |
| 2021/0374958 A1* | 12/2021 | Nakano ............. G06F 18/24317 |
| 2022/0013089 A1 | 1/2022 | Kreeger et al. |
| 2022/0071582 A1 | 3/2022 | DeFreitas et al. |
| 2023/0215059 A1* | 7/2023 | Ayvali ................... G06T 17/00 |

FOREIGN PATENT DOCUMENTS

| | | |
|---|---|---|
| WO | 2018189551 A1 | 10/2018 |
| WO | 2019104252 A1 | 5/2019 |

OTHER PUBLICATIONS

Haarburger et al., Multi Scale Curriculum CNN for Context-Aware Breast MRI Malignancy Classification, arXIV:1906.06058v2, Jun. 17, 2019, 8 pages.

Harvey et al., The Role of Deep Learning in Breast Screening, Current Breast Cancer Reports, 2019, 11(1):17-22.

He et al., Deep Residual Learning for Image Recognition, arXiv:1512.03385, Dec. 10, 2015, 12 pages.

James et al., Evaluation of a Computer-Aided Detection (CAD)-Enhanced 2D Synthetic Mammogram: Comparison with Standard Synthetic 2D Mammograms and Conventional 2D Digital Mammography, Clinical Radiology, 2018, 73(10):886-892.

Jung et al., Detection of Masses in Mammograms Using a One-Stage Object Detector Based on a Deep Convolutional Neural Network, PloS ONE, 2018, 13(9):e0203355, pp. 1-16.

Kyono et al., MAMMO: A Deep Learning Solution for Facilitating Radiologist-Machine Collaboration in Breast Cancer Diagnosis, arXiv:1811.02661, Oct. 30, 2018, pp. 1-18.

Lehman et al., National Performance Benchmarks for Modern Screening Digital Mammography: Update from the Breast Cancer Surveillance Consortium, Radiology, 2017, 283(1):49-58.

(56) References Cited

OTHER PUBLICATIONS

Lin et al., Focal Loss for Dense Object Detection, arXiv:1708.02002, Feb. 7, 2018, pp. 1-10.
Mendel et al., Transfer Learning with Convolutional Neural Networks for Lesion Classification on Clinical Breast Tomosynthesis, Medical Imaging 2018: Computer-Aided Diagnosis, Proc. of SPIE, vol. 10575, pp. 1-6.
Rodriguez-Ruiz et al., Detection of Breast Cancer with Mammography: Effect of an Artificial Intelligence Support System, Radiology, 2019, 290(2):305-314.
Svahn, Digital Mammography and Digital Breast Tomosynthesis. Breast Cancer Screening and Diagnosis: A Synopsis, 2015, pp. 65-91.
PCT International Search Report and Written Opinion, PCT/US2020/057319, Jan. 27, 2021, 15 pages.
PCT International Search Report and Written Opinion, PCT/US2020/066912, Mar. 15, 2021, 19 pages.
Conant et al., Improving Accuracy and Efficiency with Concurrent Use of Artificial Intelligence for Digital Breast Tomosynthesis, Radiology: Artificial Intelligence, 2019, 1(4):e180096, pp. 1-12.
Geras et al., High-Resolution Breast Cancer Screening with Multi-View Deep Convolutional Neural Networks, arXiv:1703.07047, 2017, pp. 1-8.
Kooi et al., Large Scale Deep Learning for Computer Aided Detection of Mammographic Lesions, Medical Image Analysis, 2017, 35:303-312.
Lotter et al., A Multi-Scale CNN and Curriculum Learning Strategy for Mammogram Classification, arXiv:1707.06978, 2017, pp. 1-8.
Ribli et al., Detecting and Classifying Lesions in Mammograms with Deep Learning, Scientific Reports, 2018, 8:4165, pp. 1-7.
Rodriguez-Ruiz et al., Stand-Alone Artificial Intelligence for Breast Cancer Detection in Mammography: Comparison with 101 Radiologists, JNCI: Journal of the National Cancer Institute, 2019, 111(9):916-922.
Wu, K. et al., Validation of a Deep Learning Mammography Model in a Population with Low Screening Rates, arXiv:1911.00364, 2019, pp. 1-6.
Wu, N. et al., Deep Neural Networks Improve Radiologists' Performance in Breast Cancer Screening, IEEE Transactions on Medical Imaging, 2020, 39(4):1184-1194.
Yala et al., A Deep Learning Mammography-Based Model for Improved Breast Cancer Risk Prediction, Radiology, 2019, 292(1):60-66.
Shin, S. et al., Joint Weakly and Semi-Supervised Deep Learning for Localization and Classification of Masses in Breast Ultrasound Images, IEEE Transactions on Medical Imaging, 2019, 38(3):762-774.
European Patent Office, Extended Search Report, Application No. 20904783.6, Jan. 3, 2024, 11 pages.

* cited by examiner

SYSTEMS AND METHODS FOR ANALYZING TWO-DIMENSIONAL AND THREE-DIMENSIONAL IMAGE DATA

CROSS REFERENCE TO RELATED APPLICATIONS

This application represents the U.S. national stage entry of International Application No. PCT/US2020/066912 filed Dec. 23, 2020, which claims the benefit of priority to U.S. Provisional Patent Application No. 62/953,033, filed Dec. 23, 2019, the contents of which are incorporated herein by reference in its entirety.

STATEMENT REGARDING FEDERALLY SPONSORED RESEARCH

Not applicable.

BACKGROUND

Breast cancer remains a global challenge, causing over six hundred thousand deaths in 2018. To achieve earlier cancer detection, health organizations worldwide recommend screening mammography, which is estimated to decrease breast cancer mortality by 20-40%. Despite the value of screening mammography, significant false positive and false negative rates along with non-uniformities in expert reader availability leave opportunities for improving quality and access.

Despite technological improvements such as digital breast tomosynthesis (DBT), studies that have reviewed mammograms where cancer was detected estimate that indications of cancer presence are visible 20-60% of the time in earlier exams that were interpreted as normal. DBT provides three-dimensional (3D) imaging of breasts, and may generate 10-150 or more two-dimensional (2D) images representing thin slices (i.e., ~1 mm thick) of the breast per view. Due to large number of slices included, DBT requires additional time as compared to two-dimensional imaging (e.g., 2D full-field digital mammography), which pressures radiologists to read faster. However, 2D imaging may not provide as much detail to medical practitioners as 3D imaging for making a cancer presence prediction.

Thus, it would be desirable to have systems and methods that more efficiently and accurately analyze 2D and/or 3D mammography data, as well as uniformly estimate malignant tumors and/or lesions using 2D and/or 3D mammography data.

SUMMARY

The present disclosure provides systems and methods for efficiently and accurately analyzing 2D and/or 3D mammography data, as well as uniformly estimating malignant tumors and/or lesions using 2D and/or 3D mammography data. In one non-limiting aspect, the present disclosure provides a computerized method for a likelihood of malignancy in breast tissue of a patient. The method includes receiving, with a computer processor, an image of the breast tissue, providing the image of the breast tissue to a model including a trained neural network; the trained neural network being previously trained by training a first neural network based on a set of annotated patches derived from a first group of two-dimensional images, each annotated patch including a patch-level label and a portion of a two-dimensional image included in the first group of two-dimensional images, initializing a second neural network based on the first neural network, training the second neural network based on a first set of annotated images, at least one annotated image included in the first set of annotated images including a two-dimensional image included in a second group of two-dimensional images, at least one bounding box, and at least one malignancy label associated with the at least one bounding box, training the second neural network based on a second set of annotated images, each annotated image included in the second set of annotated images including a two-dimensional image included in a third group of two-dimensional images and an image-level malignancy likelihood score, and outputting the second neural network as the trained neural network, receiving an indicator from the model, and outputting a report including the indicator to at least one of a memory or a display.

In the method, the image of the breast tissue may be a two-dimensional digital mammogram.

In the method, the image of the breast tissue may be a synthetic two-dimensional image generated based on a digital breast tomosynthesis image. In some configurations, the digital breast tomosynthesis image may include a plurality of slices, and the synthetic two-dimensional image may include an array of pixels, and at least a portion of the pixels included in the array of pixels may include a pixel intensity value previously generated by providing at least a portion of the plurality of slices to a second trained neural network, receiving a plurality of indicators from the trained second neural network, and each indicator included in the plurality of indicators may include a malignancy likelihood score, determining, for a target pixel included in the array of pixels, a target pixel intensity based on a first indicator included in the plurality of indicators, the first indicator including a greater malignancy likelihood score than a second indicator included in the plurality of indicators. In some configurations, at least a portion of the pixels included in the array of pixels may include a pixel intensity value previously generated by determining, for a second target pixel included in the array of pixels, no pixel included in the plurality of pixels includes a pixel location associated with the second target pixel, setting a pixel intensity included in the second target pixel equal to a default pixel included in a default slice included the plurality of slices, the default pixel including a pixel location associated with the target pixel. In some configurations, each slice included in the plurality of slices being associated with a location value, and the default slice may be associated with a medial location value. In some configurations, the digital breast tomosynthesis image may include a plurality of slices, each slice included in the plurality of slices being associated with a location value, and the synthetic two-dimensional image may be generated based on a subset of the plurality of slices associated with location values included in a predetermined range of location values. In some configurations, the subset of the plurality of slices may include about eighty percent of the plurality of slices.

In the method, the second neural network may include a backbone portion, a regression portion, and a classification portion, and the method may further include training the regression portion based on the first set of annotated images without re-training the backbone portion and the classification portion. In some configurations, the training the second neural network based on the second set of annotated images may include training the backbone portion and the classification portion without training the regression portion.

In the method, the first neural network may include a first plurality of weights and the second neural network may include a backbone portion comprising a second plurality of weights, and the initializing the second neural network based on the first neural network may include setting weights included in the second plurality of weights equal to weights included in the first plurality of weights. In some configurations, the first neural network may include a deep residual network and the second neural network may include a single-stage object detection network.

In the method, the indicator may include a patient malignancy likelihood score.

In the method, the indicator may include an area of the image of the breast tissue.

In another non-limiting aspect, the present disclosure provides a system for generating assessing a likelihood of malignancy for breast tissue of a patient. The system includes a memory configured to store an image of the breast tissue, a processor configured to access the memory and to provide the image of the breast tissue to a model including a trained neural network, the trained neural network being previously trained by training a first neural network based on a set of annotated patches derived from a first group of two-dimensional images, each annotated patch including a patch-level label and a portion of a two-dimensional image included in the first group of two-dimensional images, initializing a second neural network based on the first neural network, training the second neural network based on a first set of annotated images, at least one annotated image included in the first set of annotated images including a two-dimensional image included in a second group of two-dimensional images, at least one bounding box, and at least one malignancy label associated with the at least one bounding box, training the second neural network based on a second set of annotated images, each annotated image included in the second set of annotated images including a two-dimensional image included in a third group of two-dimensional images and an image-level malignancy likelihood score, and outputting the second neural network as the trained neural network, receive an indicator from the model, and output a report including the indicator to at least one of a memory or a display.

In the method, the image of the breast tissue may be a two-dimensional digital mammogram.

In the method, the image of the breast tissue may be a synthetic two-dimensional image generated based on a digital breast tomosynthesis image. In some configurations, the digital breast tomosynthesis image may include a plurality of slices, and the synthetic two-dimensional image may include an array of pixels, at least a portion of the pixels included in the array of pixels including a pixel intensity value previously generated by providing at least a portion of the plurality of slices to a second trained neural network, receiving a plurality of indicators from the trained second neural network, each indicator included in the plurality of indicators comprising a malignancy likelihood score, and determining, for a target pixel included in the array of pixels, a target pixel intensity based on a first indicator included in the plurality of indicators, the first indicator a greater malignancy likelihood score than a second indicator included in the plurality of indicators. In some configurations, at least a portion of the pixels included in the array of pixels may include a pixel intensity value previously generated by determining, for a second target pixel included in the array of pixels, no pixel included in the plurality of pixels includes a pixel location associated with the second target pixel, setting a pixel intensity included in the second target pixel equal to a default pixel included in a default slice included the plurality of slices, the default pixel including a pixel location associated with the second target pixel. In some configurations, each slice included in the plurality of slices may be associated with a location value, and the default slice may be associated with a medial location value. In some configurations, the digital breast tomosynthesis image may include a plurality of slices, each slice included in the plurality of slices being associated with a location value, and the synthetic two-dimensional image may be generated based on a subset of the plurality of slices associated with location values included in a predetermined range of location values. In some configurations, the subset of the plurality of slices may include about eighty percent of the plurality of slices.

In the method, the second neural network may include a backbone portion, a regression portion, and a classification portion, and the method may further include training the regression portion based on the first set of annotated images without re-training the backbone portion and the classification portion. In some configurations, the training the second neural network based on the second set of annotated images may include training the backbone portion and the classification portion without training the regression portion.

In the method, the first neural network may include a first plurality of weights and the second neural network comprises a backbone portion comprising a second plurality of weights, and the initializing the second neural network based on the first neural network may include setting weights included in the second plurality of weights equal to weights included in the first plurality of weights.

In the method, the first neural network may include a deep residual network and the second neural network may include a single-stage object detection network.

In the method, the indicator may include a patient malignancy likelihood score.

In the method, the indicator may include an area of the image of the breast tissue.

In yet another non-limiting aspect, the present disclosure provides a method for determining a malignancy likelihood score for breast tissue of a patient. The method includes receiving an image of the breast tissue, providing the image of the breast tissue to a model including a trained neural network. The trained neural network is previously trained by training a first neural network based on a set of annotated patches derived from a first group of two-dimensional images, each annotated patch includes a malignancy likelihood score and a portion of a two-dimensional image included in the first group of two-dimensional images, initializing a second neural network based on the first neural network, training the second neural network based on a first set of annotated images, at least one annotated image included in the first set of annotated images includes a two-dimensional image included in a second group of two-dimensional images, at least one bounding box, and at least one malignancy likelihood score associated with the at least one bounding box, training the second neural network based on a second set of annotated images, each annotated image included in the second set of annotated images includes a two-dimensional image included in a third group of two-dimensional images and an image-level malignancy likelihood score, and outputting the second neural network as the trained neural network, receiving the malignancy likelihood score from the model, and outputting a report including the patient malignancy likelihood score to at least one of a memory or a display.

In a further non-limiting aspect, the present disclosure provides a system for generating a malignancy likelihood score for breast tissue of a patient. The system includes a memory configured to store an image of the breast tissue, and a processor configured to access the memory and to provide the image of the breast tissue to a model including a trained neural network; the trained neural network being previously trained by training a first neural network based on a set of annotated patches derived from a first group of two-dimensional images, each annotated patch includes a malignancy likelihood score and a portion of a two-dimensional image included in the first group of two-dimensional images, initializing a second neural network based on the first neural network, training the second neural network based on a first set of annotated images, at least one annotated image included in the first set of annotated images includes a two-dimensional image included in a second group of two-dimensional images, at least one bounding box, and at least one malignancy likelihood score associated with the at least one bounding box, training the second neural network based on a second set of annotated images, each annotated image included in the second set of annotated images including a two-dimensional image included in a third group of two-dimensional images and an image-level malignancy likelihood score, and outputting the second neural network as the trained neural network, receive the malignancy likelihood score from the model, and output a report including the malignancy likelihood score to at least one of a memory or a display.

DETAILED DESCRIPTION

As will be described herein, exemplary systems and method for efficiently and uniformly displaying relevant regions of two-dimensional (2D) mammography data and/or three-dimensional (3D) tomography data, as well as determining malignancy in the 2D mammography data and/or 3D tomography data using machine learning techniques are provided.

Approaches other than the systems and methods described below may exist for analyzing relevant regions of 2D mammography data and/or 3D tomosynthesis data, and/or determining malignancy of tumors and/or lesions of breast tissue, all with drawbacks. One approach is to have a human practitioner label relevant regions of every slice included in a 3D mammogram. Human-based approaches can be costly and slow, especially for a 3D mammogram due to the extensive time taken to label each 2D slice by a human practitioner. Additionally, human-based approaches can be inconsistent due to differing preferences/expertise levels between human practitioners and to differing amounts of information available to aid in human labeling (i.e., radiology reports, pathology reports, etc.).

Another approach is to train a machine learning model that receives an entire 3D tomography dataset (i.e., every slice included in the 3D tomography dataset) and outputs a malignancy likelihood score indicating malignancy of tumors and/or lesions present in the breast tissue. This approach can be an infeasible due to the size of the data and memory limits of a data processing system, and may also be prone to overfitting.

Yet another approach may involve randomly choosing a slice from a set of 2D slices sampling or choosing a default slice (i.e., a twenty-fifth slice or middle slice) of a set of 2D slices, and training a machine learning model to output a malignancy likelihood score based on the slice. This approach may also be prone to overfitting because the slice would likely not contain a tumor and/or lesion, if present.

Still another approach may involve training a machine learning model using only weakly labeled or strongly labeled training data, which may not provide accurate enough prediction of malignancy and/or relevant regions to be clinically useful. Training on only strongly labeled data can limit the amount of data for which the model can be trained, thus limiting accuracy; whereas training on only weakly labeled data can cause overfitting and poor generalization performance.

Figure 1:
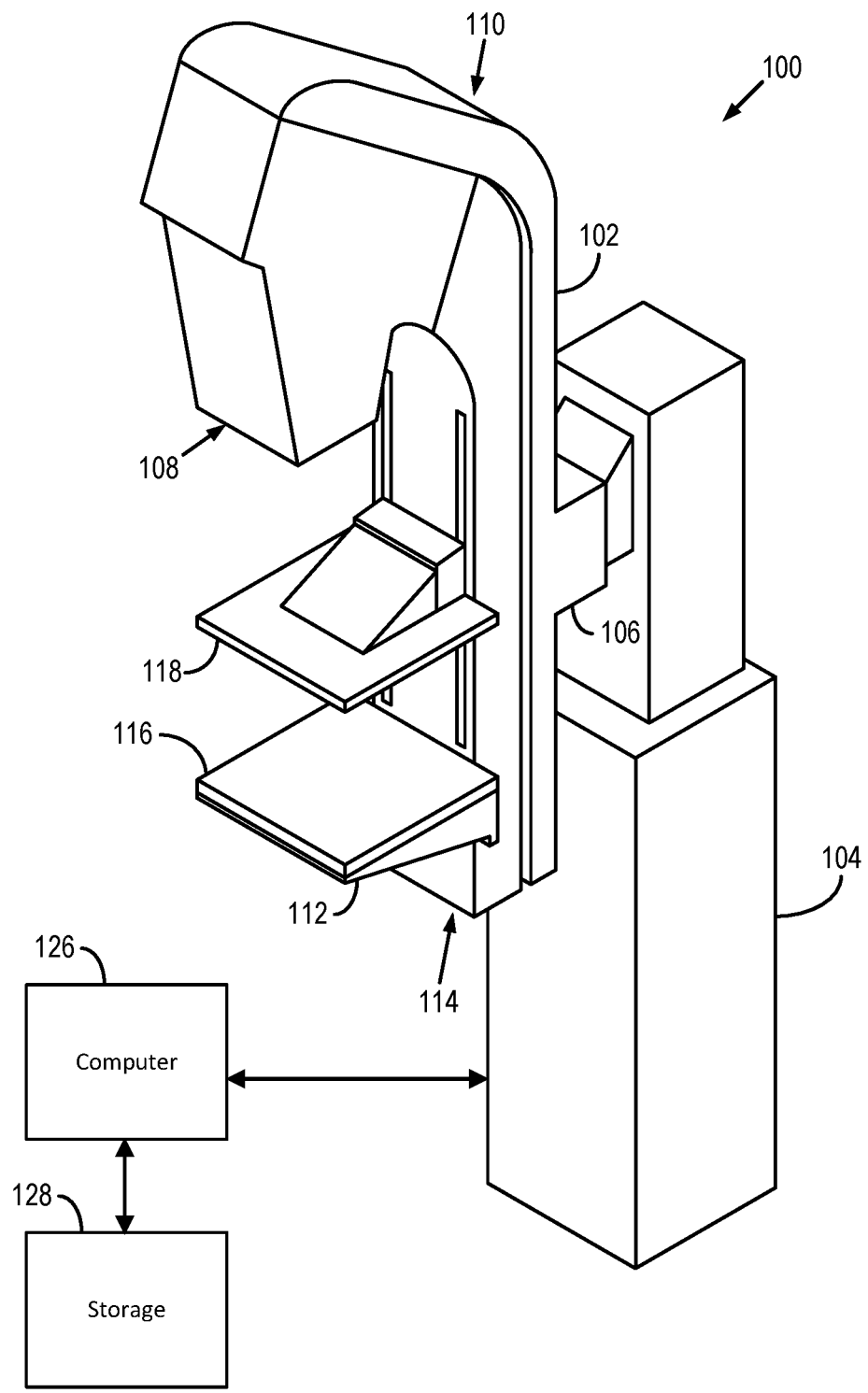
FIG. 1 is a block diagram that shows an exemplary x-ray imaging system.

Referring to FIG. 1, an example of an x-ray imaging system 100, such as a 3D digital breast tomosynthesis (DBT) system, is shown. The x-ray imaging system 100 can include an x-ray source assembly 108 coupled to a first end 110 of an arm 102. An x-ray detector assembly 112 can be coupled proximate an opposing end 114. The x-ray source assembly 108 may extend substantially perpendicular to the arm 102 and be directed toward the x-ray detector assembly 112. The x-ray detector assembly 112 also extends from the arm 102 such that the x-ray detector assembly 112 receives x-ray radiation produced by the x-ray source assembly 108, transmitted through the breast, and incident on the x-ray detector assembly 112. A breast support plate 116, and a breast compression plate 118, are positioned between the x-ray source assembly 108 and the x-ray detector assembly 112. The x-ray source assembly 108 may be stationary or movable. The x-ray imaging system 100 can generate a reconstructed image including 3D DBT data. The 3D DBT data can include a number of 2D slices. In some configurations, the reconstructed image can include 3D tomography data including a plurality of 2D slices having a thickness of about 1 mm. The 2D slices can be used to create a synthetic 2D image, which will be described below. In some configurations, the x-ray imaging system 100 can generate intermediate two-dimensional "slabs," representing, for example, maximum intensity projections of a subset of 2D slices. For example, a single maximum intensity projection slab can be generated from ten slices, and multiple slabs can be generated from a plurality of slices, such as ten slabs from one hundred slices. The reconstructed image can be applied as an input to a computer 126 which stores the image in a mass storage device 128, which can include a memory. The computer 126 may also provide commands to the x-ray imaging system 100 in order to control the generation of the reconstructed image.

Figure 2:
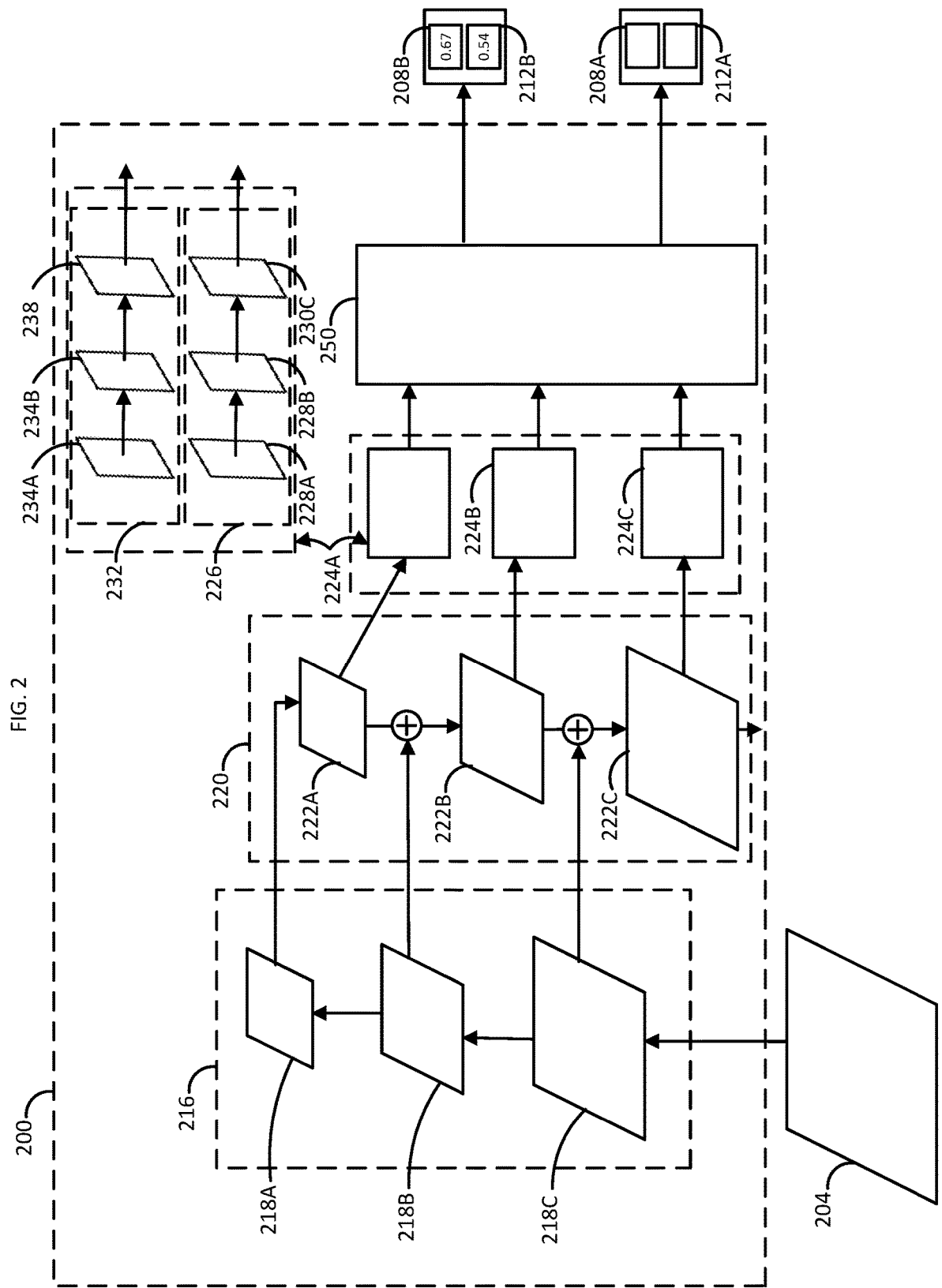
FIG. 2 is a block diagram that shows an exemplary embodiment of a model for generating regions of interest for a two-dimensional image.

Referring to FIG. 2, an exemplary embodiment of a model 200 for generating regions of interest (ROIs) for an input two-dimensional (2D) image 204 is shown. The ROIs may be referred to as indicators. In some configurations, the 2D image 204 can be a native 2D mammogram image (e.g., an image generated by a 2D full-field digital mammography system), a synthetic 2D mammogram image (e.g., a 2D image generated based on 3D image data), and/or a 2D slice of 3D DBT data.

The model 200 can accept the 2D image 204 and output any number of ROIs, for example, a first ROI including a first area 208A and a first score 208B, and a second ROI including a second area 212A and a second score 212B. In some configurations, each ROI can be associated with a slice number indicating a 2D slice that the ROI was generated based on, for example a fourth slice of a set of seventy-five 2D slices. The slice number can be used when selecting and/or combining ROIs to create a synthetic image, as will be explained below. Depending on the characteristics of the 2D image 204, such as when the 2D image 204 is deemed to not have any regions that sufficiently indicate a potential malignancy, zero ROIs may be output. Each ROI can include an area that can be a subregion of the 2D image 204. As noted above, each 2D image can be formatted as an array of pixels. The subregion can be a subset of the array of pixels. In some configurations, the model 200 can include one or more neural networks configured to detect objects within 2D images. The objects can be ROIs.

In some configurations, the model 200 can output ROI's that follow a predetermined shape. For example, rectangular bounding boxes can be used to encompass a potential candidate for a tumor or lesion. It is contemplated that irregular shapes (e.g., a "blob" of pixels) can be used to better outline potential tumors or lesions. When creating a training database of ROIs, one or more human practitioners may find it more intuitive to use rectangular bounding boxes than other shapes. Neural networks that use segmentation mask-based approaches to identify objects could be used to output predicted ROIs with irregular shapes. The model 200 can then be trained to identify rectangular-shaped ROIs including a subarray of the pixels included in the 2D image 204. The pixels of the ROI can include one or more color intensity values (e.g., a white intensity value) and a location within the 2D image 204 (e.g., the pixel at a given (x, y) location in a 2000×1500 pixel slice). While some mammography imaging systems produce greyscale images of breast tissue, it is appreciated that the model can be used with colorized 2D images.

In addition to the subarray of pixels, the ROI can include a relevancy score indicating how relevant the subarray of pixels is to determining a malignancy likelihood score. The relevancy score can be used to create a synthetic 2D image using one or more ROIs and/or generate a malignancy likelihood score for a patient, as will be explained in detail below. The relevancy score can be selected from a range of values such as between 0 and 1. When identifying ROIs for a training dataset, a human practitioner can assign relevancy scores for each ROI within the range of the values. The human practitioner could alternatively assign relevancy scores using a different scale, such as 0-100 (with higher scores indication higher potential for malignancy) which could then be normalized to relevancy score range used by the model 200. In some configurations, the human practitioner can identify ROIs as benign in order to better train the model 200 to identify potentially malignant ROIs.

In some configurations, the model 200 can include a neural network such as a convolutional neural network. In order to train the model 200, a training dataset including 2D data consisting of full-field digital mammography (FFDM) images and/or slices from a set of 3D tomosynthesis images and pre-identified (e.g., by one or more medical practitioners) ROIs can be used to train the model.

At least some of the 2D data can be strongly annotated data. Strongly annotated data can include predetermined ROIs. Human practitioners can identify ROIs by examining a given 2D image (e.g., a 2D slice or a 2D FFDM image), outlining, using a predetermined shape such as a rectangular box, any regions that may be of interest, and assign a relevancy score to the predetermined shape based on their medical expertise and/or experience in evaluating tumors and/or lesions. Alternatively, the relevancy score can be assigned based on pathology results that indicate whether or not a lesion is malignant.

At least some of the 2D data can be weakly annotated data. Weakly annotated data can include an image-level relevancy score without any bounding boxes or other outlined areas of an image. To generate the weakly annotated data, a medical practitioner can annotate a 2D image as malignant (e.g., "1"), or not malignant (e.g., "0"). For example, it can be determined through pathology that a patient's right breast contains a malignancy, and then a label of "1" can be given to every mammography image of the right breast. A large training database can be generated by having one or more medical practitioners identify (e.g., annotate) ROIs in 2D images taken from a plurality of FFDM images or slices of 3D tomosynthesis images (e.g., images of multiple patients), as well as annotate entire 2D images as malignant (e.g., "1"), or not malignant.

An advantage of using FFDM images in training data is that there are presently more publicly available annotated FFDM images than annotated 3D tomosynthesis images. Additionally, 2D images are easier to annotate than 3D tomosynthesis images, which can require annotating a large number of individual slices included in each 3D tomosynthesis image. Once trained, the model 200 can receive an input 2D slice and output one or more ROIs, each ROI including an estimated relevancy score and a subarray of pixels of the input 2D slice.

The model 200 can include a number of layers such as convolutional layers. It is understood that some configurations of the model 200 may have different numbers of layers, a different arrangement of layers or other differences. However, in all configurations, the model 200 can be capable of receiving an input 2D input slice and outputting any regions of interest associated with the input 2D input slice. The model 200 can be a one-stage detection network including one or more subnetworks. In some configurations, the model 200 can include a RetinaNet.

The model 200 can include a first subnetwork 216. The first subnetwork 216 can be a feedforward neural network with one or more layers 218A-C. In some configurations, the first subnetwork 216 can include a deep residual network ("ResNet"). In some configurations, the deep residual network can be a ResNet-50 neural network. As will be described below, the first subnetwork 216 can initially be trained independently and then integrated into the model 200. A second subnetwork 220 can be built on top of the first subnetwork to effectively create a single neural network, using the first subnetwork 216 as the backbone for the network. The first subnetwork 216 can be referred to as a backbone portion of the model 200. The second subnetwork 220 can contain a plurality of layers including a first layer 222A, a second layer 222B, and a third layer 222C, though other numbers of layers (i.e., five layers) can be used, and three layers are shown for simplicity. For example, the ResNet-50 neural network can include fifty layers.

Each of the first layer 222A, the second layer 222B, and the third layer 222C can be a convolutional layer. Each layer can be made of a number of building blocks (not shown). Each building block can include a number of parameters layers such as three parameter layers, each parameter layer including a number of filters (e.g., 256) with a given filter size (e.g., 3×3). Each of the first layer 222A, the second layer 222B, and the third layer 222C can have an associated output size such as 144×144, 72×72, and 36×36. The output sizes can vary between input slices based on pre-processing conditions and/or parameters. As the output size decreases between layers of the second subnetwork 220, the number of filters of the parameter layers can increase proportionally, i.e., halving output size results in doubling the number of filters. The second subnetwork can also include a global average pooling layer connected to a final layer (i.e., the third layer 222C), a fully-connected layer connected to the global average pooling layer, and a softmax layer connected to the fully-connected layer and having a 1×1 output size (i.e., a single value).

The model 200 can include a plurality of tertiary subnetworks such as a first tertiary network 224A, a second tertiary network 224B, and a third tertiary network 224C. Each of the tertiary networks 224A-C can be connected to a layer of the second subnetwork 220. The first tertiary network 224A can be connected to the first layer 222A, the second tertiary network 224B can be connected to the second layer 222B, and the third tertiary network 224C can be connected to the third layer 222C. Each tertiary network can receive features from a layer of the second subnetwork 220 in order to detect tumors and/or lesions at different levels of scale.

Each tertiary network can include a box regression subnetwork 226. The box regression subnetwork 226 can include one or more convolutional layers 228A-B, each followed by rectified linear (ReLU) activations, and a final convolutional layer 230 configured to output regression coordinates corresponding to anchors associated with a portion of one of the layers of the second subnetwork 220 (and corresponding to an array of pixels of the input 2D image 204). The anchors can be predetermined subarrays of the various layers of the second subnetwork 220. The regression coordinates can represent a predicted offset between an anchor and a predicted bounding box. For each bounding box included in an ROI, a set of regression coordinates (e.g. four regression coordinates) and the corresponding anchor can be used to calculate the coordinates of the bounding box. The model 200 can include a regression portion including the box regression subnetworks included in the first tertiary network 224A, the second tertiary network 224B, and the third tertiary network 224C.

Each tertiary network can include a classification subnetwork 232. The classification subnetwork 232 can include one or more convolutional layers 234A-B, each followed by ReLU activations, and a final convolutional layer 238 followed by sigmoidal activations to output predictions of object presence (i.e., malignant tumor and/or lesion presence). The classification subnetwork 232 can be used to obtain one or more estimations of whether or not a patient has a malignant tumor and/or lesion at various spatial locations of the 2D image 204. More specifically, each bounding box can be associated with an estimated score output by the classification subnetwork. In some configurations, the value of each estimated score can range from zero to one. One of the spatial locations can include an entire layer, i.e., first layer 222A, of the second subnetwork 220. In this way, the classification subnetwork 232 can output an estimation of whether or not a patient has a malignant tumor and/or lesion based on a 2D slice. It is contemplated that the final convolutional layer 238 can be followed by Softmax activations in models that are trained to classify multiple types of malignant regions, for example multiple levels of malignancy (e.g., low risk regions, high risk regions, etc.). The model 200 can include a classification portion including the classification subnetworks included in the first tertiary network 224A, the second tertiary network 224B, and the third tertiary network 224C.

The model 200 can include an output layer 250 for normalizing data across different scales, calculating bounding box coordinates, and/or filtering out low scoring bounding box predictions. The output layer 250 can receive outputs from the tertiary subnetworks 224A-C and output one or more ROIs, each ROI including an array of pixels scaled to the array size of the 2D image 204 and an associated score. The array of pixels can be a bounding box (e.g., a rectangular bounding box) calculated based on the regression coordinates and the anchors. The output layer 250 can filter out any scores below a predetermined threshold, for example, 0.5. In some configurations, the output layer 250 can receive outputs from the tertiary subnetworks 224A-C and output a single malignancy likelihood score. In some configurations, the single malignancy likelihood score can be selected to be the highest scoring bounding box score.

Figure 3:
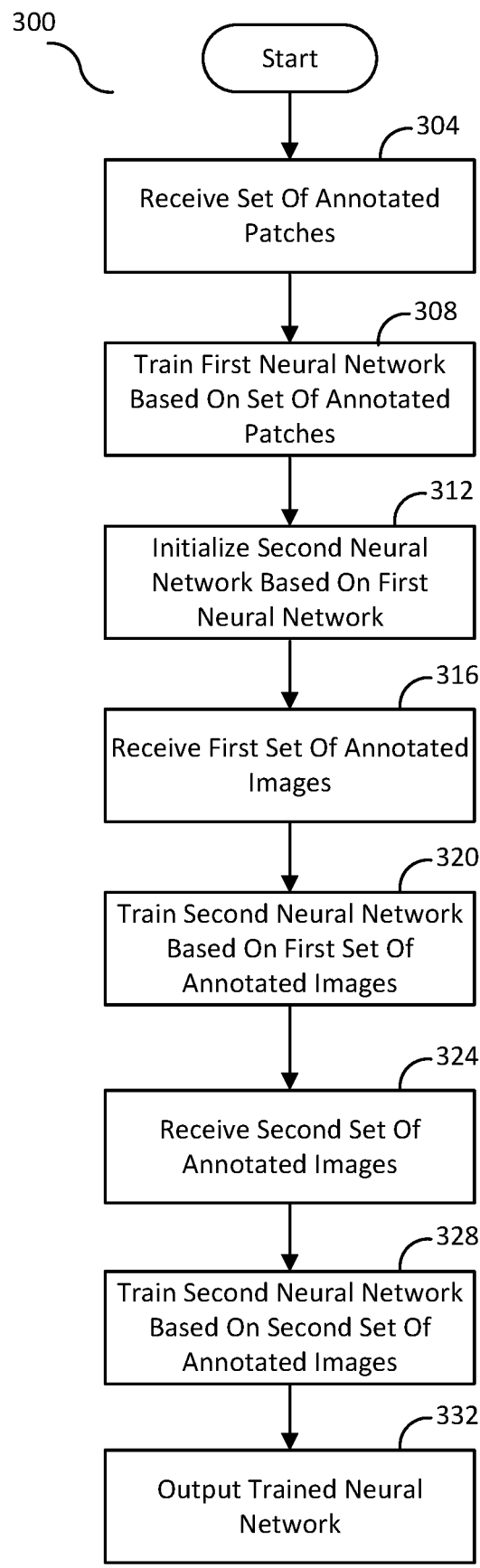
FIG. 3 is an exemplary process 300 for training a neural network.

Referring to FIG. 2 as well as FIG. 3, a process 300 for training a neural network is shown. The neural network can be included in the model 200. The process 300 can be implemented as instructions on one or more memories included in a data processing system. The data processing system can further include one or more processors in communication with the one or more memories and configured to execute the instructions. The one or more processors can be configured to access a memory, which can be included in the mass storage device 128, having training data stored thereon.

At 304, the process 300 can receive a set of annotated patches. The annotated patches can be derived from a first group of two-dimensional images (e.g., native 2D mammograms). Each annotated patch can include a label and a portion of a two-dimensional image included in the first group of two-dimensional images. Each patch can include a portion of a two dimensional image. In some configurations, to generate the set of annotated patches, the process 300 can randomly select raw patches of the two-dimensional image, and can randomly rotate patches, randomly resize patches by a factor up to 20%, and/or randomly vertically mirror patches. In some configurations, the process 300 can pre-process the raw patches by normalizing pixel values to a predetermined range (e.g., a range of [127.5, 127.5]). The randomizing and/or preprocessing can be previously performed. In some configurations, to generate patches containing lesions, the process 300 can select a random location within a lesion boundary generated by a medical practitioner as the center of the patch containing the lesion. Then, if the resulting patch includes less than a predetermined number of pixels containing the lesion mask (e.g., six pixels), the patch can be discarded and a new patch can sampled. In some configurations, the process 300 can remove any patches containing less than 10% of the breast foreground (e.g., as determined by Otsu's method and/or by thresholding using the minimal pixel value in the image) from the set of annotated patches. In some aspects, the label can indicate a lesion type (e.g., mass, calcifications, focal asymmetry, architectural distortion, or no lesion). In some aspects, the label can indicate a malignancy type (e.g., normal, benign, or malignant). The set of annotated patches can be referred to as strongly annotated. The process 300 can then proceed to 308.

At 308, the process 300 can train a first neural network based on the set of annotated patches. In some configurations, the first subnetwork 216 can include at least a portion of the first neural network. For example, the first subnetwork 216 can include at least some convolutional layers included in the first neural network, but not include a classification layer included in the first neural network. The first neural network can be a ResNet-50 neural network. The first neural network can be initialized based on ImageNet pre-trained weights. In some configurations, the process 300 can train the first neural network to classify lesion type based on patches included in the set of annotated patches that are labeled by lesion type. In some configurations, the lesion type can be mass, calcifications, focal asymmetry, architectural distortion, or no lesion. After the first neural network is trained to classify lesion type, the process 300 can train the first neural network to determine malignancy type based on patches included in the set of annotated patches that are labeled by malignancy type. In some configurations, the malignancy type can be normal, benign, or malignant. In some configurations, a batch size of sixteen can be used to train the first neural network. In some configurations, an Adam optimizer with a learning rate of 1e5 can be used to train the first neural network. The process 300 can then proceed to 312.

At 312, the process 300 can initialize a second neural network based on the first neural network. The second neural network can include one or more components of the model 200. In some configurations, the second neural network can be a single-stage object detection network (e.g., RetinaNet). In some configurations, the second neural network can include a backbone portion (e.g., the first subnetwork 216), a regression portion (e.g., the box regression subnetworks included in the first tertiary network 224A, the second tertiary network 224B, and the third tertiary network 224C), and a classification portion (e.g., the classification subnetworks included in the first tertiary network 224A, the second tertiary network 224B, and the third tertiary network 224C). In some configurations, the process 300 can initialize the backbone portion based on the first neural network. The process 300 can initialize weights included in the backbone portion based on weights included in the first neural network. The process 300 can then proceed to 316.

At 316, the process 300 can receive a first set of annotated images. The annotated images can be generated based on a second group of two-dimensional images (e.g., native 2D mammograms). Each annotated image can include one or more ROIs, each ROI including label and a bounding box included in the annotated image. In some aspects, the label can indicate a malignancy type (e.g., normal, benign, or malignant). In some configurations, the process 300 can preprocess the raw images by normalizing pixel values to a predetermined range (e.g., a range of [127.5, 127.5]) and/or normalizing the height of the images to a predetermined height (e.g., 1750 pixels). In some configurations, to generate the first set of annotated images, the process 300 can randomly resize images by a factor up to 15% and/or randomly vertically mirror images. In some configurations, the process 300 can crop out background portions of the annotated images. The randomizing and/or preprocessing can be previously performed. The first set of annotated images can be referred to as strongly annotated. The process 300 can then proceed to 320.

At 320, the process can train the second neural network based on the first set of annotated images. The process 300 can train the second neural network to generate ROIs including malignancy type and a bounding box based on the first set of annotated images that are labeled by malignancy type. In some configurations, the malignancy type can be normal, benign, or malignant. In some configurations, a batch size of one can be used to train the first neural network. In some configurations, an Adam optimizer with a learning rate of 1e5 and gradient norm clipping with a value of 0.001 can be used to train the first neural network. The process 300 can then proceed to 324.

At 324, the process 300 can receive a second set of annotated images. The annotated images can be generated based on a third group of two-dimensional images (e.g., native 2D mammograms). Each annotated image included in the second set of annotated images can include a 2D image and an image-level label. The image-level can be a binary malignancy label (e.g., malignant or not malignant). In some configurations, the process 300 can preprocess the raw images by normalizing pixel values to a predetermined range (e.g., a range of [127.5, 127.5]) and/or normalizing the height of the images to a predetermined height (e.g., 1750 pixels). In some configurations, to generate the second set of annotated images, the process 300 can randomly resize images by a factor up to 15% and/or randomly vertically mirror images. In some configurations, the process 300 can crop out background portions of the annotated images. The randomizing and/or preprocessing can be previously performed. The second set of annotated images can be referred to as weakly annotated.

At 328, the process 300 can train the second neural network based on the second set of annotated images. The second neural network, which previously was used as an object detection model, can be converted to an image classification model by changing the output layer 250 to output a maximum over all of the bounding box classification scores. In this way, the second neural network can be fully differentiable while allowing end-to-end training with binary labels. In some configurations, the process 300 can train the model using the Adam optimizer starting with a learning rate of 2.5e6, the learning rate being decreased by a factor of four at a predetermined number of iterations (e.g., every 100,000 iterations for a total of 300,000 iterations). In some configurations, the process 300 can determine that the second neural network is fully trained based on AUC performance. For example, the process 300 can determine AUC performance on a validation set of images every four thousand iterations, and determine that the second neural network is fully trained if the AUC performance decreases or stays the same. In some configurations, the process 300 can fine-tune the fully trained model after determining the model is fully trained. In some configurations, the process 300 can fine-tune the regression portion based on the first set of annotated images. More specifically, the process 300 can freeze weights included in the backbone portion and the classification portion of the trained model, and train only the regression portion. In this way, the process 300 can allow the regression portion to adapt to any change in the weights in the backbone portion during the previous training on the second set of annotated images, where the regression portion is not updated. In some configurations, the process 300 can train the trained model for a predetermined number (e.g., 50,000) of iterations with a predetermined learning rate (e.g., 2.5e6) using the same preprocessing and data augmentation techniques as described above. The process 300 can then proceed to 332.

At 332, the process 300 can output a trained neural network. The trained neural network can include the second trained neural network. The process 300 can cause the trained neural network to be stored (e.g., in a memory). The process 300 can then end.

Figure 4:
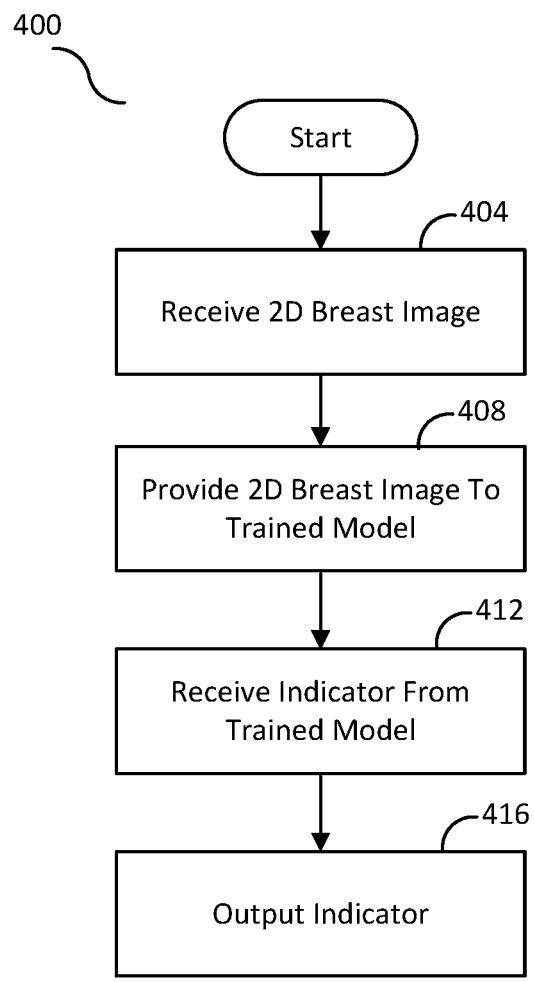
FIG. 4 is an exemplary process for generating a malignancy indicator based a 2D breast image.

Referring now to FIGS. 1, 2, and 3 as well as FIG. 4, a process 400 for generating a malignancy indicator based a 2D breast image is shown. The process 400 can be implemented as instructions on one or more memories included in a data processing system. The data processing system can further include one or more processors in communication with the one or more memories and configured to execute the instructions. The one or more processors can be configured to access a memory, which can be included in the mass storage device 128, having 2D breast images stored thereon.

At 404, the process 400 can receive a 2D breast image. The 2D breast image can be a native 2D mammogram image (e.g., an image generated by a 2D full-field digital mammography system). The 2D breast image can be associated with a patient. The process 400 can then proceed to 408.

At 408, the process 400 can provide the 2D breast image to a trained model. The trained model can include the trained neural network generated using the process 300. The process 400 can then proceed to 412.

At 412, the process 400 can receive an indicator from the trained model. In some configurations, the indicator can include a patient malignancy likelihood score and an area of the 2D breast image. The area of the 2D breast image can be associated with a bounding box generated by the trained model, and the patient malignancy likelihood score can be associated with a malignancy of the area of the 2D breast image, which may include a lesion. In some configurations, the indicator can include a patient malignancy score associated with the entire 2D breast image (i.e., an image level score). Components of the indicator can be modified based on a practitioner's preferences by modifying the output layer 250. In some configurations, the process 400 can receive a plurality of indicators (e.g., if the 2D breast image has multiple lesions). The process 400 can then proceed to 416.

At 416, the process 400 can output the indicator to a memory for storage and/or use by another process, and/or to a display such as a computer monitor for viewing by a human practitioner. For example, the process 400 can output the indicator to a display in a medical facility to allow a medical practitioner to view the indicator and potentially determine a diagnosis of a patient based on the indicator. The indicator may be stored in a database of medical records for future analysis and/or studies of breast cancer patients. In some configurations, the process 400 can also output one or more of the indicators received at 412 for storage and/or use by another process, and/or to a display such as a computer monitor for viewing by a human practitioner. The process 400 may output the indicator as a report. The process 400 can then end.

Figure 5:
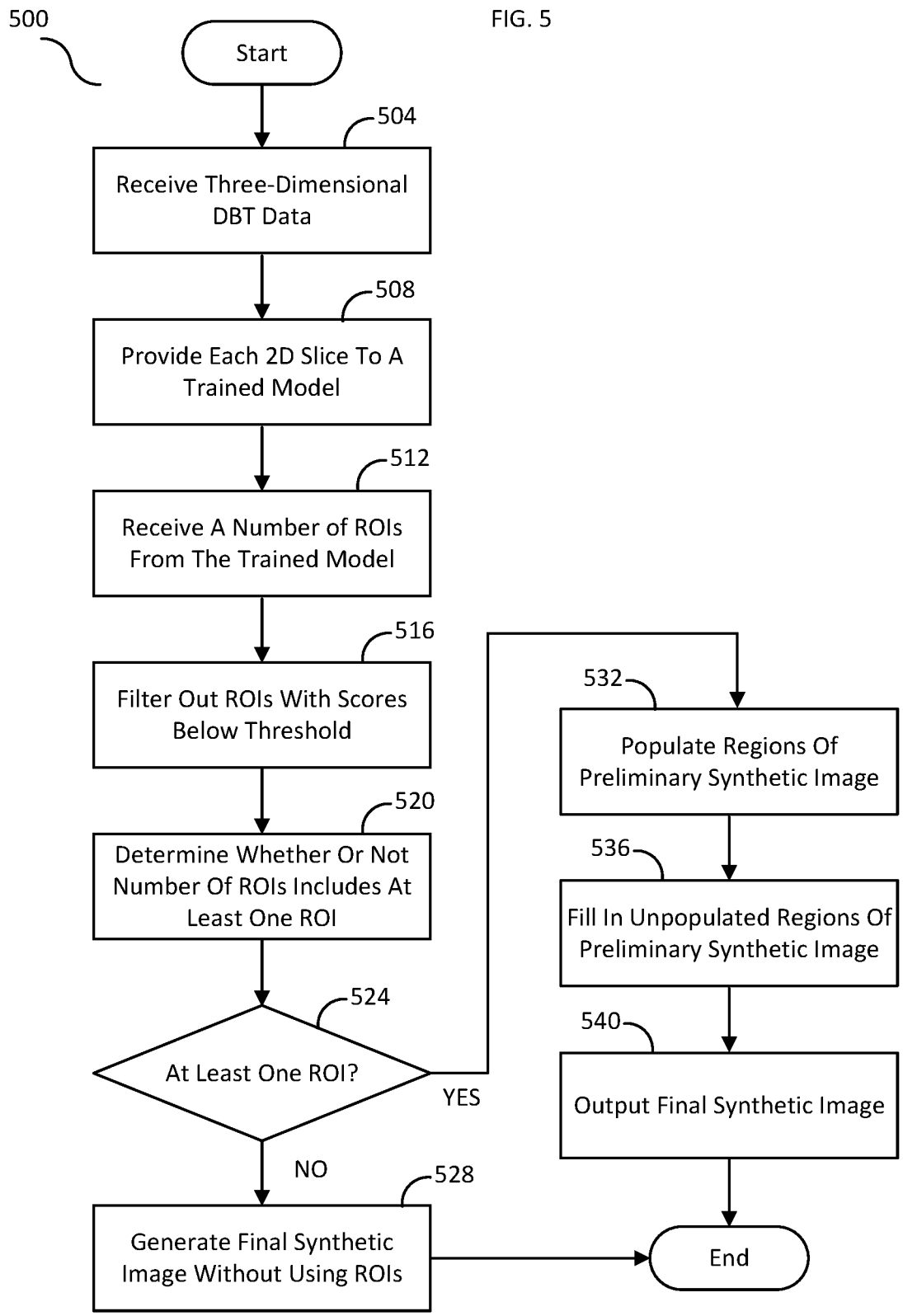
FIG. 5 is an exemplary process for creating a synthetic image using a model trained to detect ROIs in 2D slices of 3D tomosynthesis data.

Referring to FIGS. 1 and 2 as well as FIG. 5, a process 500 for creating a synthetic image using a model trained to detect ROIs in 2D slices of 3D tomosynthesis data is shown. The process 500 can include one or more steps for selecting one or more of the most relevant ROIs output from the model and using the ROIs to create the synthetic image. The process 500 can be implemented as instructions on one or more memories included in a data processing system. The data processing system can further include one or more processors in communication with the one or more memories and configured to execute the instructions. The one or more processors can be configured to access a memory, which can be included in the mass storage device 128, having 3D tomosynthesis data including a number of two-dimensional slices stored thereon.

At 504, the process 500 can receive 3D tomosynthesis data of breast tissue of a patient. The 3D tomosynthesis data can be generated by a 3D mammography imaging system such as the x-ray imaging system 100. The 3D tomosynthesis data can include a number of 2D slices corresponding to a predetermined thickness, such as 1 mm, of the breast tissue. Depending on the patient and/or imaging system, the 3D tomosynthesis data may include about 10-150 2D slices or more. Each 2D slice can be associated with a slice number indicative of the location of the 2D slice within the number of 2D slices. Each 2D slice can be an array of pixels of a predetermined size, such as 2000×1500 pixels. The process 500 can then proceed to 508.

At 508, the process 500 can individually provide each of a number of the 2D slices to a trained model capable of detecting ROIs based on the 2D slices. The trained model can be the model 200 described above. In some configurations, a subset of the 2D slices, such as slices associated with a range of slice numbers, can be provided to the model. The range of slice numbers can include a middle percentage of the 2D slices. For example, the subset of slices can include the middle eighty percent of the 2D slices (e.g., slices ten through ninety of one hundred slices). Using a middle range of the 2D slices can help remove noisy images found near the ends of DBT stacks. In some configurations, the trained model can be trained based on an image dataset including two-dimensional full-field digital mammography images annotated by a medical practitioner. In some configurations, the trained model can be trained using the process described in conjunction with FIG. 4. The process 500 can then proceed to 512.

At 512, the process 500 can receive, for each 2D slice provided to the model, a number of ROIs the model outputs. The model may output zero ROIs, one ROI, or a plurality of ROIs. Depending on the 2D slices and/or the model, a majority of the slices may not have any ROIs. As described above, the ROI can include a score and a subarray of the pixels of the 2D slice, each pixel having an intensity value and a location within the 2D slice. Each ROI can be associated with a slice number indicating which 2D slice of the 3D tomosynthesis data the ROI was generated from. The process 500 can then proceed to 516.

At 516, the process 500 can filter out any ROIs that have a score below a predetermined threshold value from the number of ROIs. The threshold value can be selected in order to include more or less ROIs in a final synthetic image (by selecting a lower or higher threshold value respectively), to reduce potential false negatives (by selecting a lower value), and/or in order to reduce potential false positives (by selecting a higher value). For example, a user could select a threshold value of 0.5 if the score can range between 0 and 1. The process 500 can then remove any ROIs that have a score below 0.5 from the number of ROIs. The process 500 can then proceed to 520. In some configurations, the process 500 may proceed from 512 to 520 without filtering out any ROIs (e.g., the threshold value is zero).

At 520, the process 500 can determine whether or not the number of ROIs contains at least one ROI. The process 500 can then proceed to 524.

At 524, the process 500 can proceed to 528 in response to determining that the number of ROIs does not include at least one ROI ("NO" at 524). Alternatively, the process 500 can proceed to 532 in response to determining that the number of ROIs includes at least one ROI.

At 528, the process 500 can generate the final synthetic image without using any ROIs. In some configurations, the process can select a default slice of the 2D slices included in the 3D tomosynthesis data to use as the final synthetic image. The default slice can be a middle slice of the 2D slices (e.g., the thirty-eighth slice of seventy-five 2D slices). The pixels of the default slice can then be included as the pixels of the final synthetic image. The process 500 can then end.

At 532, the process 500 can populate regions of a preliminary synthetic image with one or ROIs included in the number of ROIs. The preliminary synthetic image can be an array the same size as the final synthetic image initialized with null values for each of the pixel intensity values. The process 500 can then add one or more ROIs to the preliminary synthetic image. The ROIs can be added based on one or more criteria. In some configurations, the process can determine the ROI with the highest score for each pixel location. The intensity value of the preliminary synthetic image at the pixel location can then be set equal to the intensity value of the ROI at the pixel location. In other words, the process 532 can utilize a maximum suspicion technique to populate the preliminary synthetic image. In the case that multiple ROIs have the same score at a given pixel location, the ROI with the largest number of pixels, the largest number of pixels encircling the pixel location, and/or the highest intensity value at the pixel location can be selected as the ROI for the pixel location. In some configurations, the preliminary synthetic image can be populated based using non-maximum suppression (NMS) based on an intersection-over-union (IOU) threshold (e.g., an IOU of 0.2). If multiple ROIs overlap at a given pixel, the process 500 may "suppress" all the ROIs except for the highest scoring ROI by not using the lower scoring ROIs to populate the preliminary synthetic image. For example, ROIs with scores of 0.85 and 0.75 could be used to populate the preliminary image. The ROI with the score of 0.85 may overlap a lower scoring ROI with a score of 0.65 (e.g., occupy at least one of the same pixel locations as the ROI with a score of 0.65) and the ROI with the score of 0.75 may not overlap the ROI with a score of 0.65. Each pixel of the preliminary synthetic image can also be associated with the slice number of the ROI used to populate the given intensity value of the given pixel. The process 500 can then proceed to 536.

At 536, the process 500 can fill in unpopulated regions of the preliminary synthetic image. In some configurations, the process 500 can fill in unpopulated regions of the preliminary synthetic image based on a default slice. In some configurations, the process can select a default slice of the 2D slices included in the 3D tomosynthesis data to use to fill in unpopulated regions of the preliminary synthetic slice. The default slice may be a middle slice of the 2D slices (e.g., the thirty-eighth slice of seventy-five 2D slices). The process 500 can then proceed to 540.

At 540, the process 500 can output the final synthetic image to a memory for storage and/or use by another process, and/or to a display such as a computer monitor for viewing by a human practitioner. The process 500 can then end.

Figure 6:
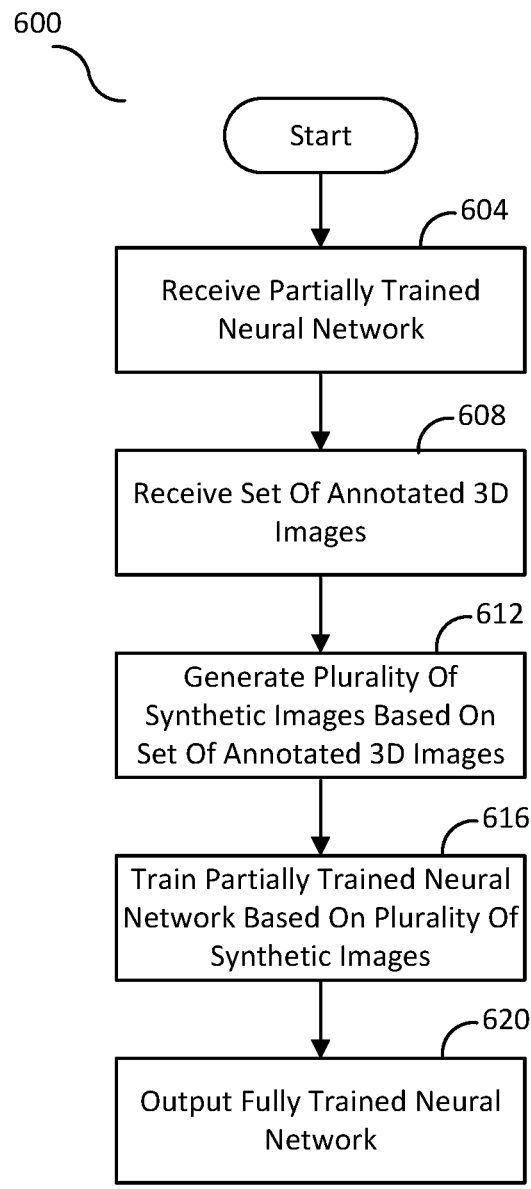
FIG. 6 is another exemplary process for training a neural network.

Referring now to FIGS. 1-5 as well as FIG. 6, another process 600 for training a neural network is shown. In particular, the process 600 can train a neural network to detect malignancy based on 3D images. The neural network can be included in the model 200. The process 600 can be implemented as instructions on one or more memories included in a data processing system. The data processing system can further include one or more processors in communication with the one or more memories and configured to execute the instructions. The one or more processors can be configured to access a memory, which can be included in the mass storage device 128, having training data stored thereon.

At 604, the process 600 can receive a partially trained neural network. The partially trained neural network can be the second trained neural network after 320 and/or 328 in the process 300. In other words, the partially trained neural network can be trained based on the first set of annotated images. The process 600 can then proceed to 608.

At 608, the process 600 can receive a set of annotated 3D images. In some configurations, each 3D image included in the set of annotated 3D images can be a DBT image labeled with an image-level label. The image-level can be a binary malignancy label (e.g., malignant or not malignant). The second set of annotated images can be referred to as weakly annotated. The process 600 can then proceed to 612.

At 612, the process 600 can generate a plurality of synthetic images. In some configurations, the process 600 can generate each synthetic image included in the plurality of synthetic images using the process 500 in conjunction with the set of annotated 3D images. For example, the process 500 can generate a maximum suspicion 2D image for every 3D image included in the set of annotated 3D images. Each synthetic image can be associated with the label associated with the 3D image used to generate the synthetic image. The process 600 can then proceed to 616.

At 616, the process 600 can train the partially trained neural network based on the plurality of synthetic images. The partially trained neural network, which previously was used as an object detection model, can be converted to an image classification model by changing the output layer 250 to output a maximum over all of the bounding box classification scores. In this way, the partially trained neural network can be fully differentiable while allowing end-to-end training with binary labels. In some configurations, the process 600 can train the model using the Adam optimizer starting with a learning rate of 2.5e6, the learning rate being decreased by a factor of four at a predetermined number of iterations. The process 600 may train the partially trained neural network for fewer iterations than the second trained neural network is trained in the process 600 due to less DBT data being available. In some configurations, the process 600 can determine that the second neural network is fully trained based on AUC performance. For example, the process 600 can determine AUC performance on a validation set of images every four thousand iterations, and determine that the partially trained neural network is fully trained if the AUC performance decreases or stays the same. In some configurations, the process 600 can fine-tune the fully trained model after determining the model is fully trained. In some configurations, the process 600 can fine-tune the regression portion based on the 2D set of annotated images. More specifically, the process 600 can freeze weights included in the backbone portion and the classification portion of the trained model, and train only the regression portion. In this way, the process 600 can allow the regression portion to adapt to any change in the weights in the backbone portion during the previous training on the second set of annotated images, where the regression portion is not updated. In some configurations, the process 600 can train the trained model for a predetermined number (e.g., 50,000) of iterations with a predetermined learning rate (e.g., 2.5e6)

using the same preprocessing and data augmentation techniques as described above. The process 600 can then proceed to 620.

At 620, the process 600 can output a trained neural network. The trained neural network can include the fully-trained neural network generated at 616. The process 600 can cause the trained neural network to be stored (e.g., in a memory). The process 600 can then end.

Figure 7:
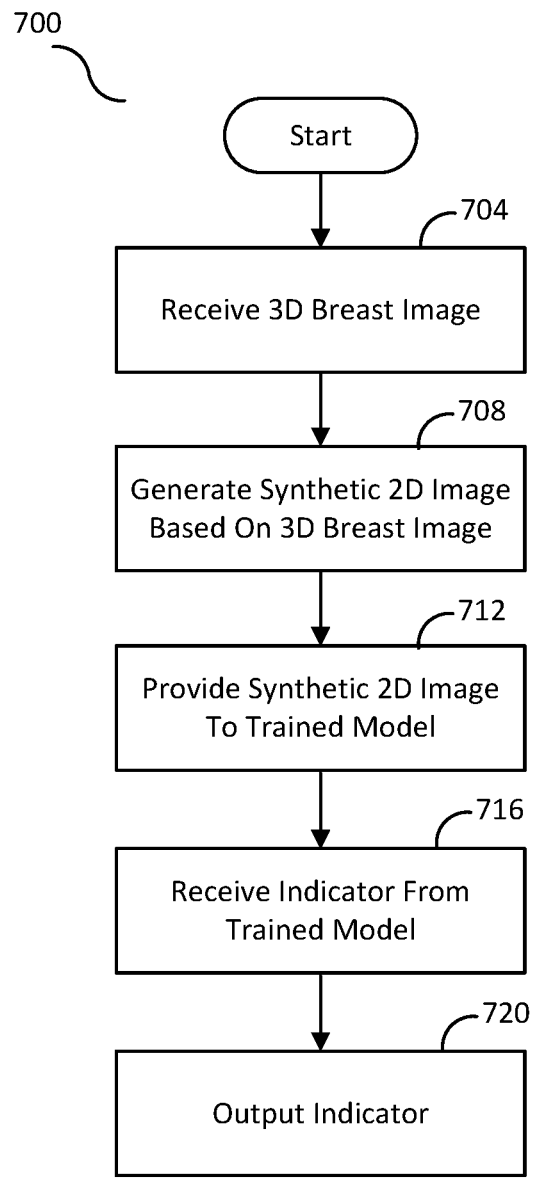
FIG. 7 is an exemplary process for generating a malignancy indicator based a 3D breast image.

Referring now to FIGS. 1, 2, 5, and 6 as well as FIG. 7, a process 700 for generating a malignancy indicator based a 3D breast image is shown. The process 600 can be implemented as instructions on one or more memories included in a data processing system. The data processing system can further include one or more processors in communication with the one or more memories and configured to execute the instructions. The one or more processors can be configured to access a memory, which can be included in the mass storage device 128, having 3D breast images stored thereon.

At 704, the process 700 can receive a 3D breast image. The 3D breast image can be a DBT image. The 3D breast image can be associated with a patient. The process 700 can then proceed to 708.

At 708, the process 700 can generate a synthetic 2D image based on the 3D breast image. The process 700 can generate the synthetic 2D image using the process 500. The process 700 can then proceed to 712.

At 712, the process 700 can provide the synthetic 2D image to a trained model. The trained model can include the trained neural network generated using the process 600. The process 700 can then proceed to 716.

At 716, the process 700 can receive an indicator from the trained model. In some configurations, the indicator can include a patient malignancy likelihood score and an area of the synthetic 2D image. In some configurations, the area of the synthetic image and/or pixels can be associated with one or more slice numbers indicative of the original slice(s) used to generate the synthetic 2D image. In this way, a practitioner can view one or more slices including lesions. In some configurations, the indicator can include a ranked ordering of slices used to generate the area of the synthetic 2D image (e.g., slices ordered by percentage of the area of the synthetic 2D image generated based on a given slice). In this way, the practitioner can view the most relevant slices. The area of the synthetic 2D image can be associated with a bounding box generated by the trained model, and the patient malignancy likelihood score can be associated with a malignancy of the area of the synthetic 2D image, which may include a lesion. In some configurations, the indicator can include a patient malignancy score associated with the entire synthetic 2D image (i.e., an image level score). Components of the indicator can be modified based on a practitioner's preferences by modifying the output layer 250. In some configurations, the process 700 can receive a plurality of indicators (e.g., if the synthetic 2D image has multiple lesions). The process 700 can then proceed to 720.

At 720, the process 700 can output the indicator to a memory for storage and/or use by another process, and/or to a display such as a computer monitor for viewing by a human practitioner. For example, the process 700 can output the indicator to a display in a medical facility to allow a medical practitioner to view the indicator and potentially determine a diagnosis of a patient based on the indicator. The indicator may be stored in a database of medical records for future analysis and/or studies of breast cancer patients. In some configurations, the process 700 can also output one or more of the indicators received at 716 for storage and/or use by another process, and/or to a display such as a computer monitor for viewing by a human practitioner. The process 700 may output the indicator as a report. The process 700 can then end.

Testing

In testing, models trained in conjunction with the process 300 were shown to outperform human practitioners as well as some alternative predictive approaches. Table 1 summarizes the data sources used to train and test the models. In addition to the datasets OMI-DB and DDSM, datasets were collected from three US clinical sites for training, denoted as Sites A, B, and C. The data used for testing includes test partitions of the OMI-DB and "Site A—DM" datasets in addition to three datasets that were never used for model training or selection. These testing-only datasets include a screening DM (digital mammography, e.g. 2D mammography) dataset from a Massachusetts health system used for a reader study (Site D), a diagnostic DM dataset from an urban hospital in China (Site E), and a screening DBT dataset from a community hospital in Oregon (Site A—DBT). It is noted that testing on screening mammograms was performed whenever possible, but the low screening rates in China necessitate using diagnostic exams (i.e., those in which the woman presents with symptoms) in the Site E dataset.

TABLE 1

| Dataset | Location | Modality | Manufacturer | Train | Test |
|---|---|---|---|---|---|
| DDSM | United States | Film (2D) | Film | X | |
| OMI-DB | United Kingdom | DM | Hologic | X | X |
| Site A - DM | Oregon | DM | GE | X | X |
| Site A - DBT | Oregon | DBT | Hologic | | X |
| Site B | Rhode Island | DBT | Hologic | X | |
| Site C | Oregon | DBT | Hologic | X | |
| Site D | Massachusetts | DM | Hologic | | X |
| Site E | China | DM | Hologic | | X |

A reader study was conducted using both "index" and "pre-index" cancer exams to directly compare to expert radiologists in both regimes. Specifically, the index exams are defined as mammograms acquired up to three months prior to biopsy-proven malignancy. Pre-index exams are defined as those that were acquired 12-24 months prior to the index exams and interpreted as negative in clinical practice. Following the BIRADS standard, a BIRADS score of 1 or 2 was considered a negative interpretation and a "confirmed negative" was further defined as a negative exam followed by an additional BIRADS 1-2 screen. All negatives used in the reader study were confirmed negatives.

Figure 8:
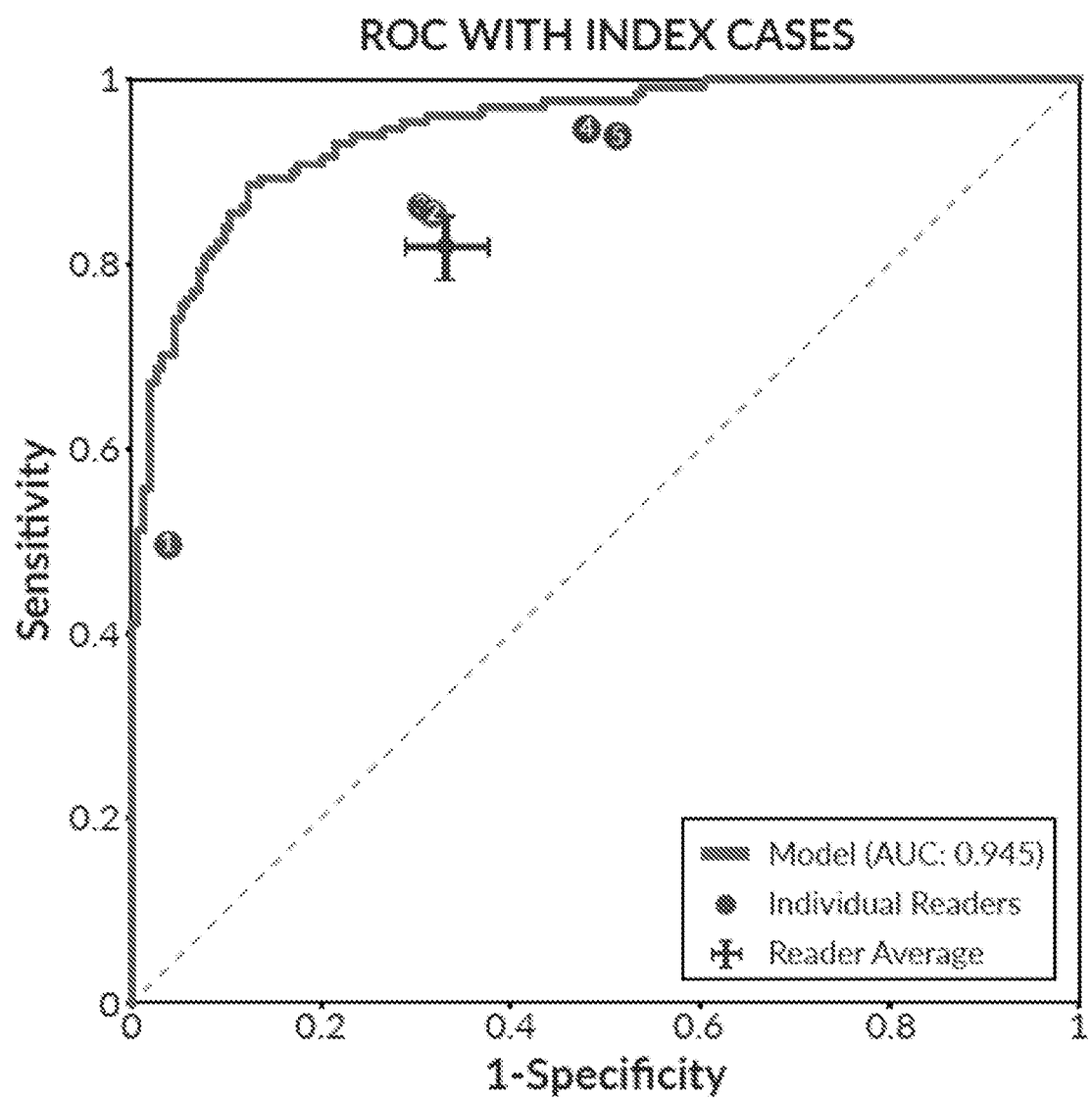
FIG. 8 is a receiver operating characteristic (ROC) plot that summarizes results of an "index" component of a reader study.

FIG. 8 is a receiver operating characteristic (ROC) plot that summarizes the results of the "index" component of the reader study. The study involved five radiologists, each fellowship-trained in breast imaging and practicing full-time in the field. The data consisted of screening DM cases retrospectively collected from a regional health system located in a different US state than any of the sources of training data. FIG. 8 is a ROC plot based on case-level performance comparing the readers to a deep learning model trained using the disclosed techniques on the set of 131 index cancer exams and 154 confirmed negatives. The points representing each reader all fall below the model's ROC curve, indicating that the model outperformed all five radiologists. At the average reader specificity, the model achieved an absolute increase in sensitivity of 14.2% (95% confidence interval (CI): 9.2-18.5%; p<0.0001). At the average reader sensitivity, the model achieved an absolute increase in specificity of 24.0% (95% CI: 17.4-30.4%;

p<0.0001). Reader ROC curves based on a continuous "probability of malignancy" score were also generated and illustrated similar higher performance by the model. Additionally, the model outperformed every simulated combination of the readers and also compares favorably to other recently published models on this dataset.

Figure 9:
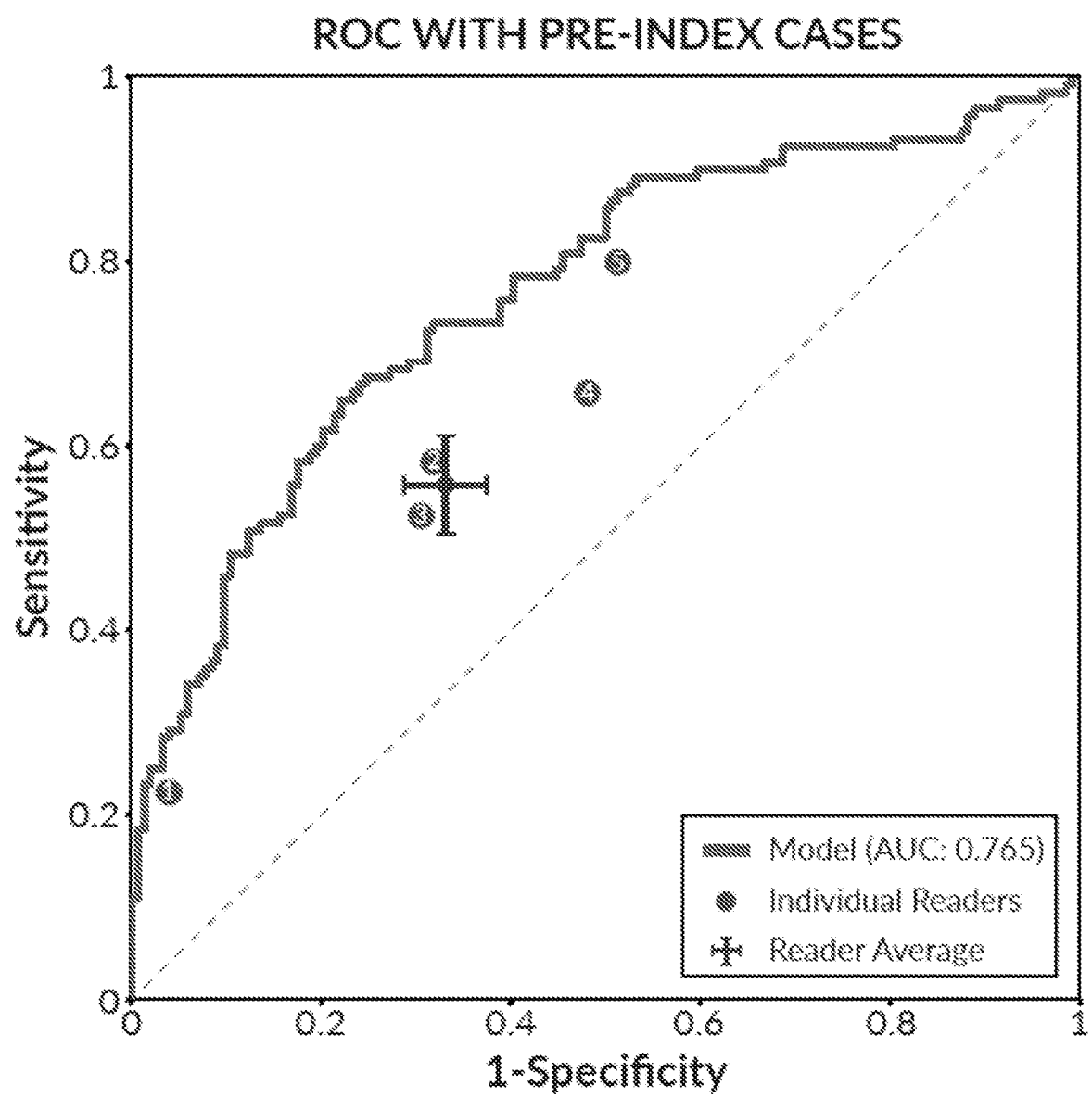
FIG. 9 is a ROC plot that summarizes a second component of the reader study involving "pre-index" exams from the same patients.

FIG. 9 is a ROC plot that summarizes the second component of the reader study involving "pre-index" exams from the same patients. FIG. 9 was generated based on a dataset including 120 pre-index cancer exams—which are defined as mammograms interpreted as negative 12-24 months prior to the index exam in which cancer was found—and 154 confirmed negatives. Pre-index exams can largely be thought of as challenging false negatives, as studies estimate that breast cancers typically exist 3+ years prior to detection by mammography. The deep learning model outperformed all five readers in the early detection, pre-index paradigm as well. The absolute performances of the readers and the model were lower on the pre-index cancer exams than on the index cancer exams, which is expected given the difficulty of these cases. Nonetheless, the model still demonstrated an absolute increase in sensitivity of 17.5% (95% CI: 6.0-26.2%; p=0.0009) at the average reader specificity, and an absolute increase in specificity of 16.2% (95% CI: 7.3-24.6%; p=0.0008) at the average reader sensitivity. At a specificity of 90%, the model would have flagged 45.8% (95% CI: 28.8-57.1%) of the pre-index (e.g., "missed") cancer cases for additional workup. The model additionally exhibited higher performance than recently published models on the pre-index dataset.

Given the interpretable localization outputs of the model, it is also possible to evaluate sensitivity while requiring correct localization. For both laterality-level and quadrant-level localization, the model again demonstrates improvements in sensitivity for both the index and pre-index cases in the reader study. The trend of higher model performance also holds when considering factors such as lesion type, cancer type, cancer size, and breast density.

Building upon the reader study performance, standalone performance was evaluated on larger, diverse datasets spanning different populations, equipment manufacturers, and modalities. These results are summarized in Table 2, which are calculated using index cancer exams.

Site A (254 cancers, 7,697 negatives) datasets. Rows 3-4 show performance on a dataset collected at a Chinese hospital (Site E; 533 cancers, 1,000 negatives). The dataset consists entirely of diagnostic exams given the low prevalence of screening mammography in China. Nevertheless, even when adjusting for tumor size using bootstrap resampling to approximate the distribution of tumor sizes expected in an American screening population, the model still achieves high performance (Row 7). Rows 5-7 show performance on DBT data (Site A—DBT; 78 cancers, 518 negatives). Row 5 contains results of the 2D model fine-tuned on the manufacturer-generated synthetic 2D images, which are created to augment/substitute DM images in a DBT study (*indicates this fine-tuned model). Row 6 contains the results of the weakly-supervised 3D model trained using the process 600, illustrating strong performance when evaluated on the synthetic images generated via process 500 computed from the DBT slices. It is noted that when scoring the DBT volume as the maximum bounding box score over all of the slices, the strongly-supervised 2D model used to create the synthetic images exhibits an AUC of 0.865+−0.020. Thus, fine-tuning this model on the synthetic images created according to process 500 significantly improves its performance. Row 7 show results when combining predictions across the final 3D model trained in accordance with process 600 and the 2D model trained in accordance with process 300. The standard deviation for each AUC value was calculated via bootstrapping.

Beginning with a test partition of OMI-DB including 1,205 cancers and 1,538 confirmed negatives, a model trained using the disclosed techniques exhibits strong performance on DM exams from a UK screening population with an AUC of $0.963 \pm 0.003$ ($0.961 \pm 0.003$ using all 1,976 negatives—confirmed and unconfirmed). On a test partition of the Site A—DM dataset with 254 cancers and 7,697 confirmed negatives, the model achieves an AUC of $0.927 \pm 0.008$ ($0.931 \pm 0.008$ using all 16,369 negatives), which is not statistically different from the results on the other tested US screening DM dataset (Site D; p=0.22). The Site A—DM dataset consists of mammograms acquired using GE equipment, as opposed to the Hologic equipment used for the majority of the other datasets.

TABLE 2

| Dataset | Location | Manufacturer | Model | Input Type | AUC |
| --- | --- | --- | --- | --- | --- |
| OMI-DB | UK | Hologic | 2D | DM | 0.963 ± 0.003 |
| Site A- DM | Oregon | GE | 2D | DM | 0.927 ± 0.008 |
| Site E | China | Hologic | 2D | DM | 0.971 ± 0.005 |
| Site E (resampled) | China | Hologic | 2D | DM | 0.956 ± 0.020 |
| Site A - DBT | Oregon | Hologic | 2D* | DBT manufacturer synthetics | 0.922 ± 0.016 |
| Site A - DBT | Oregon | Hologic | 3D | DBT slices | 0.947 ± 0.012 |
| Site A - DBT | Oregon | Hologic | 2D + 3D | DBT manufacturer synthetics + slices | 0.957 ± 0.010 |

In Table 2, all results correspond to using the "index" exam for cancer cases and "confirmed" negatives for the non-cancer cases, except for Site E where the negatives are unconfirmed. Rows 1-2: show performance of the 2D deep learning model trained using the process 300 on held-out test sets of the OMI-DB (1,205 cancers, 1,538 negatives) and To further test the generalizability of a model trained in accordance with the process 400, performance was assessed on a DM dataset collected at an urban Chinese hospital (Site E). Testing generalization to this dataset is particularly meaningful given the low screening rates in China and the known (and potentially unknown) biological differences found in mammograms between Western and Asian populations, including a greater proportion of women with dense breasts in Asian populations. The model, which was evaluated locally at the Chinese hospital, generalized well to this population, achieving an AUC of 0.971±0.005 (using all negatives—"confirmation" is not possible given the lack of follow-up screening). Even when adjusting for tumor size to approximately match the statistics expected in an American screening population, the model achieved 0.956±0.020 AUC.

Finally, a model trained in accordance with the process 600 approach performs well when evaluated at a site not used for DBT model training. The model achieved an AUC of 0.947±0.012 (with 78 cancers and 519 confirmed negatives; 0.950±0.01 using all 11,609 negative exams). If the strongly-supervised 2D model is instead fine-tuned on the manufacturer-generated synthetic 2D images that are generated by default with each DBT study, the resulting model achieves 0.922±0.016 AUC on the test set (0.923±0.015 AUC using all negatives). Averaging predictions across the manufacturer-generated synthetic images and synthetic images generated in accordance with process 500 results in an overall performance of 0.957±0.010 (0.959±0.008 using all negatives).

Methods

Dataset Descriptions

Details of all utilized datasets described in Table 1 are provided below. All non-public datasets were collected under IRB approval and were de-identified prior to model training and testing. Within each data source, data splits were created at the patient level, meaning that exams from a given patient were all in the same split. Splits consist of training, model selection, and testing, where the model selection split is used to choose final models and determine when to stop model training. Rules for label assignment and case selection for training data varied slightly across datasets given variability in collection time periods and available metadata (as described below). However, the definitions of testing sets and label criteria were standardized across datasets unless otherwise stated. The following definitions were used in assigning labels.

Index Cancer—A mammogram obtained within the three months preceding a cancer diagnosis.

Pre-Index Cancer—A mammogram interpreted as BIRADS category 1 or 2 and obtained 12-24 months prior to an index exam.

Negative—A mammogram interpreted as BIRADS 1 or 2 from a patient with no known prior or future history of breast cancer.

Confirmed Negative—A negative exam followed by an additional BIRADS 1 or 2 interpretation at the next screening exam 9-39 months later (which represents 1-3 years of follow-up depending on the screening paradigm with a 3 month buffer). The time window was extended beyond three years to include triennial screening (e.g., the UK). Throughout, "pre-index" cases were treated as positives because, while it is not guaranteed that a pathology-proven cancer could have been determined with appropriate follow-up, it is likely that cancer existed at the time of acquisition for the vast majority of these exams.

All datasets shared the same algorithm for creating test sets, except Site D (which is described in detail in the corresponding section below). Studies were labelled as 'index', 'pre-index', 'confirmed negative', 'unconfirmed negative', or 'none' based on the aforementioned criteria. For each patient in the test set, one study was chosen in the following order of descending priority: 'index', 'pre-index', 'confirmed negative', 'unconfirmed negative'. If a patient had multiple exams with the chosen label, one exam was randomly sampled. If a patient had an index exam, a single pre-index exam was also included when available. For all training and testing, only craniocaudal (CC) and mediolateral oblique (MLO) mammographic views were used. All test sets include only screening exams (i.e., screening index cancers, screening negatives, etc.) except for Site E, where all tested exams are diagnostic given the low screening rates in China. It is noted that the proportion of confirmed versus unconfirmed negatives varies by site largely because of differing time periods of exam acquisition (i.e., not enough time may have passed for confirmation), screening paradigms, and/or BIRADS information collection ranges. Performance is reported using both confirmed and unconfirmed negatives when possible to consider results on a stringent definition of negative while also evaluating on larger amounts of data.

For training, labeling amounts to assigning each training instance (e.g., an image or bounding box) a label of '1' for cancer and '0' for non-cancer. The chief decision for assigning images a label of '1' (cancer) is in the time window allowed between cancer confirmation (biopsy) and image acquisition. For USA datasets, this window is set to 15 months. This time window was chosen to balance the risk of overfitting while still including some pre-index cancer exams for training. Localization annotations were not available for the USA datasets (except DDSM which only has index cancers), so extending the time window further could lead to overfitting on more subtle cancers. Nonetheless, the mix of yearly and bi-yearly screening in the US enables the inclusion of some pre-index cancers using a 15-month time window. For the OMI-DB from the UK, this window is extended by a year since the dataset includes a high proportion of strongly-labeled data and because the standard screening interval is longer in the UK. For non-cancers, unless otherwise noted, screening negative exams (BIRADS 1 or 2) from patients with no history of cancer were used and, when available, pathology-confirmed benign cases from patients with no history of cancer. For the pathology-confirmed benign cases, training was performed on both screening and diagnostic exams. For cancers, both screening and diagnostic exams were additionally included for training. It was found that training on diagnostic exams can improve performance even when evaluating only on screening exams (and vice versa). The only dataset where training only on screening exams was performed was the Site A—DM dataset, where lack of benign biopsy information would entail that all of the diagnostic exams to be included in training would be cancers, so diagnostics were excluded altogether to avoid such bias. As opposed to model testing where only one exam per patient is included, all qualified exams for a given patient were used for training. Below, additional details of the datasets are provided.

Digital Database of Screening Mammography (DDSM)

DDSM is a public database of scanned film mammography studies from the United States containing cases categorized as normal, benign, and malignant with verified pathology information. The dataset includes radiologist-drawn segmentation maps for every detected lesion. The data was split into 90%/10% training/model selection splits, resulting in 732 cancer, 743 benign, and 807 normal studies for training. No data from DDSM was used for testing given that it is a scanned film dataset.

OPTIMAM Mammography Imaging Database (OMI-DB)

The OMI-DB is a publicly available dataset from the UK, containing screening and diagnostic digital mammograms primarily obtained using Hologic equipment. The unique list of patients was split into 60%/20%/20% training/model selection/testing splits. This results in a training set of 5,233 cancer studies (2,332 with bounding boxes), 1,276 benign studies (296 with bounding boxes), and 16,887 negative studies. It is noted that although the proportion of positives to negatives in OMI-DB is much higher than the ratio expected in a screening population, the positives and negatives themselves are randomly sampled from their respective populations. Thus, given the invariance of ROC curves to incidence rates, bias is not expected in the test set AUC in this population compared to the full population with a natural incidence rate.

Site A

Site A is a community hospital in Oregon. The dataset from Site A primarily consists of screening mammograms, with DM data from 2010-2015 collected almost entirely from GE equipment, and DBT data from 2016-2017 collected almost entirely from Hologic equipment. For the DM data, 40% of the patients were used for training, 20% were used for model selection, and 40% were used for testing. The DBT data was used solely for testing, given its high proportion of screening exams compared to the other utilized DBT datasets. Ground truth cancer status for both modalities was obtained using a local hospital cancer registry. A radiology report also accompanied each study and contained BIRADS information. For the DBT data, a list of benigns was additionally provided by the hospital, but such information was not available for the DM data. Given the extent of longitudinal data present in the DM dataset and the lack of confirmed benign pathology information for this data, the non-cancers were chosen more strictly for training, specifically requiring the negatives to have no record of non-screening procedures or non-normal interpretations for the patient for 18 months prior to and following the exam. This results in 466 cancer studies and 48,248 negative studies for training in the Site A—DM dataset.

Site B

Site B consists of an inpatient medical center and affiliated imaging centers in Rhode Island. The data from this site contains DBT mammograms from Hologic equipment, with a mix of screening and diagnostic exams collected retrospectively between 2016-2017. Cancer status, benign results, and BIRADS were determined using a local database. The list of unique patients was split into 80%/20% training/model selection splits. Given the relatively smaller amount of DBT available for training and the desire to test on datasets not used for training, Site B was solely used for model development. The training split consists of 13,767 negative cases, 379 benign cases, and 263 cancer cases. The manufacturer-generated synthetic 2D images were also included in the weakly-supervised training for the final 2D model.

Site C

Site C is a health system in Oregon separate from the one in Site A. From Site C, DBT cases were retrospectively collected between 2017-2018. The data consists of a mix of screening and diagnostic cases acquired almost entirely using Hologic equipment. The unique list of patients was split into 70%/30% training/model selection splits. A regional cancer registry was used to determine cancer status. Like Site B, Site C was used solely for model development. Historical BIRADS information was not readily available for all the cases in Site C, so cases from patients with no entry in the regional cancer registry were used as non-cancers for training. Given the geographic proximity of Site C and Site A, a small number of patients that overlap in both sets were used when performing testing on Site A. It is noted that the manufacturer-generated synthetic 2D images were also included in the weakly supervised training for the final 2D model.

Site D

Data from Site D was used for the reader study and consisted of 405 screening DM exams that were collected retrospectively from a single health system in Massachusetts with four different imaging collection centers. No data from this site was ever used for model training or selection. The exams included in the study were acquired between July 2011 and June 2014. Out of the 405 studies, 154 were negative, 131 were index cancer exams, and 120 were pre-index cancer exams. All of the negatives were confirmed negatives. The index cancer exams were screening mammograms interpreted as suspicious and confirmed to be malignant by pathology within three months of acquisition. The pre-index exams came from the same set of women as the index exams and consisted of screening exams that were interpreted as BIRADS 1 or 2 and acquired 12-24 months prior to the index exams. All studies were acquired using Hologic equipment. Case selection was conducted over several steps. First, the cancer patients included in the study were selected by taking all patients with qualifying index and pre-index exams over the specified time period using a local cancer registry. Due to PACS limitations, it was not possible to obtain some pre-index cases. Next, the non-cancer cases were chosen to have a similar distribution in patient age and breast density compared to the cancer cases using bucketing. In total, 154 non-cancer, 131 index cancer, and 120 pre-index cancer mammograms were collected from 285 women.

Site E

Site E consists of a dataset from an urban hospital in China collected retrospectively from a contiguous period between 2012-2017. Over this time period, all pathology-proven cancers were collected along with a uniformly random sample of non-cancers, resulting in 533 cancers, 1,000 negatives (BIRADS 1 or 2 interpretation), and 100 pathology-proven benigns. Due to the low screening rates in China, the data came from diagnostic exams (i.e., exams where the patient presented with symptoms), so the distribution of tumor sizes from the cancer cases contained more large tumors (e.g. 64% larger than 2 cm) than would be expected in a typical United States screening population. To better compare to a US screening population, results on Site E were also calculated using a bootstrap resampling method to approximately match the distribution of tumor sizes from a US population according to the National Radiology Data Registry. Using this approach, a mean AUC was computed over 5K bootstrapped populations. Site E was solely used for testing and never for model development. Furthermore, the deep learning system was evaluated locally at the hospital and data never left the site.

Model Development and Training

In the testing described above, the first stage of training for the model used in testing consisted of patch-level classification (e.g., 308 in FIG. 3). Patches of size 275×275 pixels were created from the DDSM and OMI-DB datasets after the original images were resized to a height of 1750 pixels. Data augmentation was also used when creating the patches, including random 360 degree rotations, image resizing by up to 20%, and vertical mirroring. Preprocessing consisted of normalizing pixel values to a range of [−127.5, 127.5]. When creating patches containing lesions, a random location within the lesion boundary was selected as the center of the patch. If the resulting patch had fewer than 6 pixels containing the lesion mask, the patch was discarded and a new patch was sampled. For all patches, if the patch contained less than 10% of the breast foreground, as determined by Otsu's method for DDSM and by thresholding using the minimal pixel value in the image for OMI-DB, then the patch was discarded. In total, two million patches were created with an equal number of patches with and without lesions. For the patch classification model, the ResNet-50 network was used. The patch-based training stage itself consisted of two training sequences. First, starting from ImageNet pre-trained weights, the ResNet-50 model was trained for five-way classification of lesion type: mass, calcifications, focal asymmetry, architectural distortion, or no lesion. Patches from DDSM and OMI-DB were sampled in proportion to the number of cancer cases in each dataset. The model was trained for 62,500 batches with a batch size of 16, sampling equally from all lesion types. The Adam optimizer was used with a learning rate of 1 e-5. Next, the patch-level model was trained for three-way classification, using labels of normal, benign, or malignant, again sampling equally from all 3 categories. The same training parameters were also used for this stage of patch-level training.

After patch-level training, the ResNet-50 weights were used to initialize the backbone portion of a popular detection model, RetinaNet, for the second stage of training: strongly-supervised, image-level training (e.g., 320 in FIG. 3). Image pre-processing consisted of resizing to a height of 1750 pixels (maintaining the original aspect ratio), cropping out the background using the thresholding methods described above, and normalizing pixel values to a range of [−127.5, 127.5]. Data augmentation during training included random resizing of up to 15% and random vertical mirroring. Given the high class imbalance of mammography (far fewer positives than negatives), class-balancing was implemented during training by sampling malignant and non-malignant examples with equal probability. This class balancing was implemented within datasets as well to prevent the model from learning biases in the different proportions of cancers across datasets. For this strongly-supervised, image-level training stage, the bounding boxes in the OMI-DB and DDSM datasets were used. Three-way bounding box classification was performed using labels of normal, benign, or malignant. The RetinaNet model was trained for 100K iterations, with a batch size of 1. The Adam optimizer was used, with a learning rate of 1 e-5 and gradient norm clipping with a value of 0.001. Default hyperparameters were used in the RetinaNet loss, except for a weight of 0.5 that was given to the regression loss and a weight of 1.0 that was given to the classification loss.

For the weakly-supervised training stage (e.g., 328 in FIGS. 3 and 616 in FIG. 6), binary cancer/no-cancer classification was performed with a binary cross entropy loss. The same image input processing steps were used as in the strongly-supervised training stage. The RetinaNet architecture was converted to a classification model by taking a maximum over all of the bounding box classification scores, resulting in a model that remains fully differentiable while allowing end-to-end training with binary labels. For 2D, training consisted of 300K iterations using the Adam optimizer, starting with a learning rate of 2.5e-6, which was decreased by a factor of 4 every 100K iterations. Final model weights were chosen by monitoring AUC performance on the validation set every 4K iterations.

For DBT, the 'maximum suspicion projection' (MSP) approach described in the process 500 is motivated by the value of DBT in providing an optimal view into a lesion that could otherwise be obscured by overlapping tissue, and by the similarity between DBT and DM images which suggests the applicability of transfer learning. Furthermore, it is especially considered that the aggregate nature of 2D mammography can help reduce overfitting compared to training end-to-end on a large DBT volume. To this end, in the weakly-supervised stage for the 3D model, the synthetic images created through process 500 ("MSP images") were created using the model resulting from 2D strongly-supervised training as described above, after an additional 50K training iterations with a learning rate of 2.5e-6. To create the MSP images, the 2D model was evaluated on every slice in a DBT stack except for the first and last 10% of slices (which are frequently noisy). A minimal bounding box score threshold was set at a level that achieved 99% sensitivity on the OMI-DB validation set. The bounding boxes over all evaluated slices were filtered using non-maximum suppression (NMS) using an intersection-over-union (IOU) threshold of 0.2. The image patches defined by the filtered bounding boxes were then collapsed into a single 2D image array representing an image optimized for further model training. Any "empty" pixels in the projection were infilled with the corresponding pixels from the center slice of the DBT stack, resulting in the final MSP images. Overall, the MSP process is akin to a maximum intensity projection (MIP) except that the maximum is computed over ROI malignancy suspicion predicted by an AI model instead of over pixel-level intensity. Training on the resulting MSP images was conducted similar to the 2D weakly-supervised approach, except that the model was trained for 100K iterations. The input processing parameters used for 2D images were reused for DBT slices and MSP images.

After weakly-supervised training for both the 2D and 3D models, fine-tuning of the regression portion of the RetinaNet architecture was performed on the strongly-labeled data used in the second stage of training. Specifically, the backbone portion and classification portion of the network are frozen and only the regression portion is updated during this fine-tuning. This allows the regression portion to adapt to any change in the weights in the backbone portion of the network during the weakly-supervised training stage, where the regression portion is not updated. For this regression fine-tuning stage, the network is trained for 50K iterations with a learning rate of 2.5e-6 using the same preprocessing and data augmentation procedures as the previous stages. Final model selection was based on performance on the held-out model selection data partition. The final model was an aggregation of three equivalently-trained models starting from different random seeds. A prediction score for a given image was calculated by averaging across the three models' predictions for both horizontal orientations of the image (i.e., an average over six scores). Regression coordinates of the bounding box anchors were additionally averaged across the three models. Each breast was assigned a malignancy score by taking the average score of all its views. Each study was assigned a score by taking the greater of its two breast-level scores.

Reader Study

The reader study was performed to directly assess the performance of the described deep learning system in comparison to expert radiologists. While a reader study is certainly an artificial setting, such studies avoid the "gatekeeper bias" inherent in retrospective performance comparison, since the ground truth of each case is established a priori in reader studies. Recent evidence also suggests that the rate of positive enrichment itself in reader studies may have little effect on reader aggregate ROC performance.

Reader Selection

Five board-certified and MQSA-qualified radiologists were recruited as readers for the reader study. All readers were fellowship trained in breast imaging and had practiced for an average of 5 years post-fellowship (range 2-12 years). The readers read an average of 6,969 mammograms over the year preceding the reader study (range of 2,921-9,260), 60% of which were DM and 40% of which were DBT.

Study Design

The data for the reader study came from Site D as described above. The study was conducted in two sessions. During the first session, radiologists read the 131 index cancer exams and 76 of the negative exams. During the second session, radiologists read the 120 pre-index exams and the remaining 78 negative exams. There was a washout period of at least 4 weeks in between the two sessions for each reader. The readers were instructed to give a forced BIRADS score for each case (1-5). BIRADS 1 and 2 were considered no recall, and BIRADS 3, 4, and 5 were considered recall. Radiologists did not have any information about the patients (such as previous medical history, radiology reports, and other patient records), and were informed that the study dataset is enriched with cancer mammograms relative to the standard prevalence observed in screening; however, they were not informed about the proportion of case types. All radiologists viewed and interpreted the studies on dedicated mammography workstations in an environment similar to their clinical practice. Readers recorded their interpretations in electronic case report forms. In addition to a forced BIRADS, readers provided breast density classification and, for each detected lesion, the lesion type, laterality, quadrant, and a 0-100 probability of malignancy score (for up to four lesions). Reader binary recall decisions using BIRADS were used for analysis because this more closely reflects clinical practice.

Localization-Based Analysis

While the main reader study results described above correspond to case-level classification performance, localization-based analysis was also performed. In the study, readers reported the breast laterality and quadrant for each lesion that was determined to warrant recall. Ground truth laterality and quadrant for malignant lesions was provided by the clinical lead of the reader study by inspecting the mammogram images along with pathology and radiology reports. For the pre-index cases, the ground truth location was set to the ground truth location of the corresponding index case, even if the lesion was deemed not visible in the pre-index exam. The deep learning model considered provides localization in the form of bounding boxes. To compare to the readers and to also act as an exercise in model output interpretability, an MQSA-qualified radiologist from a different practice than the reader study site mapped the outputted boxes of the model to breast laterality and quadrant. This radiologist was blinded to the ground truth of the cases and was instructed to estimate the location of the centroid for each given bounding box, restricting the estimation to one quadrant.

Both laterality-based and quadrant-based localization sensitivities were considered, requiring correct localization at the corresponding level in addition to recalling the case. Since the readers reported at most one lesion for the vast majority of cases (90%) and to avoid scenarios where predictions involving many locations are rewarded, primary analysis restricts the predicted locations to the location corresponding to the highest scoring lesion. For the model, this corresponds to taking the highest scoring bounding box in the highest scoring laterality. For the readers, the probability of malignancy score provided for each lesion was used to select the highest scoring location. In cases with more than one malignant lesion, a true positive was assigned if the reader or model location matched the location of any of the malignant lesions. The sensitivity of each reader was compared to the model was compared by choosing a model score threshold that matches the specificity of the given reader. The model was also compared to the reader average in a similar fashion.

Statistical Analysis

Receiver operating characteristic (ROC) curves were used throughout testing as a main evaluation method. It is noted that ROC analysis is the standard method for assessing diagnostic performance because it is invariant to the ratio of positive to negative cases, and because it allows for comparing performance across the entire range of possible recall rates (i.e. operating points). Confidence intervals and standard deviations for AUCs and average readers' sensitivity and specificity were computed via bootstrapping with 10,000 random resamples. The p-value for comparing the considered model's sensitivity and specificity with the average reader sensitivity and specificity was computed by taking the proportion of times the difference between the model and readers was less than 0 across the bootstrap resamples. Bootstrapping with 10,000 random resamples was used to compare AUC performance across datasets.

The present invention has been described in terms of one or more preferred configurations, and it should be appreciated that many equivalents, alternatives, variations, and modifications, aside from those expressly stated, are possible and within the scope of the invention.

The invention claimed is:

1. A computerized method for generating an indication of a likelihood of malignancy in breast tissue of a patient, the method comprising:

receiving, with a computer processor, an image of the breast tissue, wherein the image of the breast tissue is a synthetic two-dimensional image generated based on an image that comprises a plurality of images, each image included in the plurality of images being associated with a location value, and wherein the synthetic two-dimensional image is generated based on a subset of the plurality of images associated with location values included in a predetermined range of location values;

providing the image of the breast tissue to a model comprising a trained neural network; the trained neural network being previously trained by:

training a first neural network based on a set of annotated patches derived from a first group of two-dimensional images, each annotated patch comprising a patch-level label and a portion of a two-dimensional image included in the first group of two-dimensional images;

initializing a second neural network based on the first neural network;

training the second neural network based on a first set of annotated images, at least one annotated image included in the first set of annotated images comprising a two-dimensional image included in a second group of two-dimensional images, at least one bounding box, and at least one malignancy label associated with the at least one bounding box;

training the second neural network based on a second set of annotated images, each annotated image included in the second set of annotated images comprising a two-dimensional image included in a third group of two-dimensional images and an image-level malignancy likelihood score; and
outputting the second neural network as the trained neural network; and
receiving an indicator from the model.

2. The method of claim 1, wherein the synthetic two-dimensional image is generated based on a digital breast tomosynthesis image.

3. The method of claim 2, wherein the digital breast tomosynthesis image comprises the plurality of images, and wherein the synthetic two-dimensional image comprises an array of pixels, at least a portion of the pixels included in the array of pixels comprising a pixel intensity value previously generated by:
providing at least a portion of the plurality of images to a second trained neural network;
receiving a plurality of indicators from the trained second neural network, each indicator included in the plurality of indicators comprising a malignancy likelihood score; and
determining, for a target pixel included in the array of pixels, a target pixel intensity based on a first indicator included in the plurality of indicators, the first indicator including a greater malignancy likelihood score than a second indicator included in the plurality of indicators.

4. The method of claim 3, wherein at least a portion of the pixels included in the array of pixels comprising a pixel intensity value previously generated by:
determining, for a second target pixel included in the array of pixels, no pixel included in the plurality of pixels includes a pixel location associated with the second target pixel;
setting a pixel intensity included in the second target pixel equal to a default pixel included in a default image included the plurality of images, the default pixel including a pixel location associated with the target pixel.

5. The method of claim 4, wherein each image included in the plurality of images being associated with a location value, and wherein the default image is associated with a medial location value.

6. The method of claim 1, further comprising: outputting a report including the indicator to at least one of a memory or a display.

7. The method of claim 1, wherein the second neural network comprises a backbone portion, a regression portion, and a classification portion, and wherein the method further comprises training the regression portion based on the first set of annotated images without re-training the backbone portion and the classification portion.

8. The method of claim 7, wherein the training the second neural network based on the second set of annotated images comprises training the backbone portion and the classification portion without training the regression portion.

9. The method of claim 1, wherein the first neural network comprises a first plurality of weights and the second neural network comprises a backbone portion comprising a second plurality of weights, and wherein the initializing the second neural network based on the first neural network comprises setting weights included in the second plurality of weights equal to weights included in the first plurality of weights.

10. The method of claim 9, wherein the first neural network comprises a deep residual network and the second neural network comprises a single-stage object detection network.

11. The method of claim 1, wherein the indicator comprises a patient malignancy likelihood score.

12. The method of claim 1, wherein the indicator comprises an area of the image of the breast tissue.

13. A system for generating an indication of a likelihood of malignancy for breast tissue of a patient, the system comprising:
a memory configured to store an image of the breast tissue;
a processor configured to access the memory and to:
provide the image of the breast tissue to a model comprising a trained neural network; the trained neural network being previously trained by:
training a first neural network based on a set of annotated patches derived from a first group of two-dimensional images, each annotated patch comprising a patch-level label and a portion of a two-dimensional image included in the first group of two-dimensional images;
initializing a second neural network based on the first neural network, wherein the second neural network comprises a backbone portion, a regression portion, and a classification portion;
training the second neural network based on a first set of annotated images, at least one annotated image included in the first set of annotated images comprising a two-dimensional image included in a second group of two-dimensional images, at least one bounding box, and at least one malignancy label associated with the at least one bounding box;
training the second neural network based on a second set of annotated images, each annotated image included in the second set of annotated images comprising a two-dimensional image included in a third group of two-dimensional images and an image-level malignancy likelihood score; and
outputting the second neural network as the trained neural network;
receive an indicator from the model.

14. The system of claim 13, wherein the image of the breast tissue is a two-dimensional digital mammogram.

15. The system of claim 13, wherein the image of the breast tissue is a synthetic two-dimensional image generated based on a digital breast tomosynthesis image.

16. The system of claim 15, wherein the digital breast tomosynthesis image comprises a plurality of slices, and wherein the synthetic two-dimensional image comprises an array of pixels, at least a portion of the pixels included in the array of pixels comprising a pixel intensity value previously generated by:
providing at least a portion of the plurality of slices to a second trained neural network;
receiving a plurality of indicators from the trained second neural network, each indicator included in the plurality of indicators comprising a malignancy likelihood score; and
determining, for a target pixel included in the array of pixels, a target pixel intensity based on a first indicator included in the plurality of indicators, the first indicator including a greater malignancy likelihood score than a second indicator included in the plurality of indicators.

17. The system of claim 16, wherein at least a portion of the pixels included in the array of pixels comprising a pixel intensity value previously generated by:
determining, for a second target pixel included in the array of pixels, no pixel included in the plurality of pixels includes a pixel location associated with the second target pixel;

setting a pixel intensity included in the second target pixel equal to a default pixel included in a default slice included the plurality of slices, the default pixel including a pixel location associated with the second target pixel.

18. The system of claim 17, wherein each slice included in the plurality of slices being associated with a location value, and wherein the default slice is associated with a medial location value.

19. The system of claim 15, wherein digital breast tomosynthesis image comprises a plurality of slices, each slice included in the plurality of slices being associated with a location value, and wherein the synthetic two-dimensional image is generated based on a subset of the plurality of slices associated with location values included in a predetermined range of location values.

20. The system of claim 19, wherein the subset of the plurality of slices comprises about eighty percent of the plurality of slices.

21. The system of claim 13, wherein the processor is further configured to train the regression portion based on the first set of annotated images without re-training the backbone portion and the classification portion.

22. The system of claim 21, wherein the training the second neural network based on the second set of annotated images comprises training the backbone portion and the classification portion without training the regression portion.

23. The system of claim 13, wherein the first neural network comprises a first plurality of weights and the backbone portion comprising a second plurality of weights, and wherein the initializing the second neural network based on the first neural network comprises setting weights included in the second plurality of weights equal to weights included in the first plurality of weights.

24. The system of claim 13, wherein the first neural network comprises a deep residual network and the second neural network comprises a single-stage object detection network.

25. The system of claim 13, wherein the indicator comprises a patient malignancy likelihood score.

26. The system of claim 13, wherein the indicator comprises an area of the image of the breast tissue.

27. A method for determining a malignancy likelihood score for breast tissue of a patient, the method comprising:
receiving an image of the breast tissue;
providing the image of the breast tissue to a model comprising a trained neural network; the trained neural network being previously trained by:
training a first neural network based on a set of annotated patches derived from a first group of two-dimensional images, each annotated patch comprising a malignancy likelihood score for the annotated patch and a portion of a two-dimensional image included in the first group of two-dimensional images;
initializing a second neural network based on the first neural network, wherein the second neural network comprises a backbone portion, a regression portion, and a classification portion;
training the second neural network based on a first set of annotated images, at least one annotated image included in the first set of annotated images comprising a two-dimensional image included in a second group of two-dimensional images, at least one bounding box, and at least one malignancy likelihood score associated with the at least one bounding box;
training the second neural network based on a second set of annotated images, each annotated image included in the second set of annotated images comprising a two-dimensional image included in a third group of two-dimensional images and an image-level malignancy likelihood score; and
outputting the second neural network as the trained neural network; and
receiving the malignancy likelihood score for the breast tissue of the patient from the model.

28. The method of claim 27, wherein the first neural network comprises a first plurality of weights and the backbone portion comprises a second plurality of weights, and wherein the initializing the second neural network based on the first neural network comprises setting weights included in the second plurality of weights equal to weights included in the first plurality of weights.

29. The method of claim 28, wherein the training the second neural network based on the second set of annotated images comprises training the backbone portion and the classification portion without training the regression portion.

30. A system for generating a malignancy likelihood score for breast tissue of a patient, the system comprising:
a memory configured to store an image of the breast tissue, wherein the image of the breast tissue is a synthetic two-dimensional image generated based on an image that comprises a plurality of images, each image included in the plurality of images being associated with a location value, and wherein the synthetic two-dimensional image is generated based on a subset of the plurality of images associated with location values included in a predetermined range of location values;
a processor configured to access the memory and to:
provide the image of the breast tissue to a model comprising a trained neural network; the trained neural network being previously trained by:
training a first neural network based on a set of annotated patches derived from a first group of two-dimensional images, each annotated patch comprising a malignancy likelihood score for the annotated patch and a portion of a two-dimensional image included in the first group of two-dimensional images;
initializing a second neural network based on the first neural network;
training the second neural network based on a first set of annotated images, at least one annotated image included in the first set of annotated images comprising a two-dimensional image included in a second group of two-dimensional images, at least one bounding box, and at least one malignancy likelihood score associated with the at least one bounding box;
training the second neural network based on a second set of annotated images, each annotated image included in the second set of annotated images comprising a two-dimensional image included in a third group of two-dimensional images and an image-level malignancy likelihood score; and
outputting the second neural network as the trained neural network; and
receive the malignancy likelihood score for the breast tissue of the patient from the model.

* * * * *